US012755846B1

(12) United States Patent
Awasthi et al.

(10) Patent No.: US 12,755,846 B1
(45) Date of Patent: Oct. 6, 2026

(54) SYSTEMS AND METHODS FOR GENERATING DIAGNOSTIC INFORMATION AS A FUNCTION OF AN ELECTROCARDIOGRAM SIGNAL

(71) Applicant: Anumana, Inc., Cambridge, MA (US)

(72) Inventors: Samir Awasthi Awasthi, Boston, MA (US); Wui Ip, San Francisco, CA (US); Taylor Gold West, Cambridge, MA (US); Shahir Asfahan, Bengaluru (IN); Mohan Krishna Ranganathan, Bengaluru (IN); Animesh Agarwal, San Mateo, CA (US); Rakesh Barve, Bengaluru (IN); Simos Kedikoglou, Philadelphia, PA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 19/272,125

(22) Filed: Jul. 17, 2025

(51) Int. Cl.
*G16H 50/20* (2018.01)
*G16H 50/30* (2018.01)

(52) U.S. Cl.
CPC ............ *G16H 50/20* (2018.01); *G16H 50/30* (2018.01)

(58) Field of Classification Search
None
See application file for complete search history.

(56) References Cited

U.S. PATENT DOCUMENTS 11,119,630 B1 * 9/2021 Marchetti ................ G06N 5/04
2002/0045994 A1 * 4/2002 Hampton ............... G16H 50/20 702/66
2019/0167143 A1 * 6/2019 Li .......................... A61B 5/366
2021/0204858 A1 * 7/2021 Attia .................... A61B 5/7264
2023/0017867 A1 * 1/2023 Bancos .................... G16B 5/20
2023/0148456 A9 5/2023 Zimmerman et al.
2025/0000361 A1 * 1/2025 Soori-Arachi ......... G06Q 50/22

FOREIGN PATENT DOCUMENTS

CN 108597600 A 9/2018
CN 112951416 A 6/2021
IN 202441032474 A 5/2024
IN 202441085707 A 11/2024
IN 202441091796 A 11/2024

* cited by examiner

*Primary Examiner* — John A Pauls
(74) *Attorney, Agent, or Firm* — CALDWELL LLC

(57) ABSTRACT

A system for generating diagnostic information as a function of an electrocardiogram (ECG) signal configured to receive at least an ECG signal, receive, using a user interface, a configuration signal, wherein the configuration signal includes a selection of a configurable set of artificial intelligent (AI) models, configure a medical AI module as a function of the configuration signal, wherein configuring the medical AI module includes analyzing the at least an ECG signal using the configurable set of AI models, generate a unified output data structure as a function of one or more outputs generated by the configurable set of AI models, wherein generating a unified output data structure comprises receiving diagnostic outputs generated by each AI model of the configurable set of AI models, each diagnostic output comprising a model-specific result, organizing the processed diagnostic outputs into a structured data collection, and output the unified output data structure.

20 Claims, 8 Drawing Sheets

SYSTEMS AND METHODS FOR GENERATING DIAGNOSTIC INFORMATION AS A FUNCTION OF AN ELECTROCARDIOGRAM SIGNAL

FIELD OF THE INVENTION

The present invention generally relates to the field of early diagnostic detection. In particular, the present invention is directed to systems and methods for generating diagnostic information as a function of an electrocardiogram signal.

BACKGROUND

Existing electrocardiogram (ECG) artificial intelligence (AI) models primarily focus on disease detection without providing validated support for improving patient outcomes through early intervention. Despite advances in AI-based diagnostics, integration into preventive clinical care remains limited due to the lack of regulatory and clinical validation demonstrating benefits to long-term patient management. Conventional implementations often require multiple separate ECG analyses or longitudinal data to identify evolving risks, resulting in increased clinical workflow inefficiencies and delayed decision-making. Furthermore, current systems typically do not offer clinicians configurable diagnostic panels or unified reporting from a single ECG acquisition, constraining both operational flexibility and clinical utility. These limitations hinder the broader adoption of ECG-AI technologies in outcome-driven healthcare strategies. Moreover, the inability to tailor model selection to patient-specific diagnostic needs can lead to unnecessary execution of irrelevant models, increasing computational overhead. Systems that support configurable AI model selection can improve resource efficiency by enabling targeted analyses, conserving processing time and infrastructure bandwidth.

SUMMARY OF THE DISCLOSURE

In an aspect, a system for generating diagnostic information as a function of an electrocardiogram (ECG) signal includes at least a processor and a memory communicatively connected to the at least a processor, wherein the memory contains instructions configuring the at least a processor to receive at least an ECG signal, receive, using a user interface, a configuration signal, wherein the configuration signal includes a selection of a configurable set of artificial intelligent (AI) models, configure a medical AI module as a function of the configuration signal, wherein configuring the medical AI module includes analyzing the at least an ECG signal using the configurable set of AI models, generate a unified output data structure as a function of one or more outputs generated by the configurable set of AI models, wherein generating a unified output data structure comprises receiving diagnostic outputs generated by each AI model of the configurable set of AI models, each diagnostic output comprising a model-specific result, organizing the processed diagnostic outputs into a structured data collection, and output the unified output data structure.

In another aspect, a method for generating diagnostic information as a function of an ECG signal includes receiving at least an ECG signal, receiving, using a user interface, a configuration signal, wherein the configuration signal includes a selection of a configurable set of artificial intelligent (AI) models, configuring a medical AI module as a function of the configuration signal, wherein configuring the medical AI module includes analyzing the at least an ECG signal using the configurable set of AI models, generating a unified output data structure as a function of one or more outputs generated by the configurable set of AI models, wherein generating a unified output data structure comprises receiving diagnostic outputs generated by each AI model of the configurable set of AI models, each diagnostic output comprising a model-specific result, organizing the processed diagnostic outputs into a structured data collection, and outputting the unified output data structure.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating predictive diagnostic information as a function of a single electrocardiogram (ECG) signal using a configurable set of artificial intelligence (AI) models trained on disease-specific detection tasks. In an embodiment, the system receives a single ECG signal from a patient, analyzes the signal using the configurable set of AI models, and generates a unified output data structure containing standardized diagnostic outputs, enabling clinical review to support early intervention and improved patient outcomes.

Aspects of the present disclosure can be used to streamline clinical workflows by allowing multiple disease-specific AI models to be executed concurrently on a single ECG signal, providing clinicians with a consolidated diagnostic report from a single acquisition. Aspects of the present disclosure can also be used to support outcome-driven healthcare strategies by enabling predictive diagnostics that facilitate early clinical intervention before symptomatic disease manifestation. This is so, at least in part, because the disclosed system organizes outputs into a standardized, machine-readable format, and provides configuration capabilities allowing clinicians to select, prioritize, and review outputs from AI models relevant to the specific patient characteristics or clinical context. In some embodiments, systems and methods as disclosed herein may be configured to align with or adapt to evolving standards of care, clinical guidelines, or regulatory frameworks governing AI-based diagnostics. For example, the system may support version-controlled model repositories, configurable output formats compatible with regulatory submission standards (e.g., FDA aECG), or audit modules enabling retrospective validation of model performance under updated clinical definitions. This adaptability may enable the system to remain compliant as AI-based ECG analysis transitions from a supplemental tool to a standard diagnostic component within clinical workflows.

Aspects of the present disclosure allow for dynamic configuration of the AI diagnostic panel, enabling the addition or selection of disease-specific AI models based on patient demographic data, clinical presentation, or user preference without requiring retraining of existing models. Exemplary embodiments illustrating aspects of the present disclosure are described below in the context of several specific examples.

Figure 1:
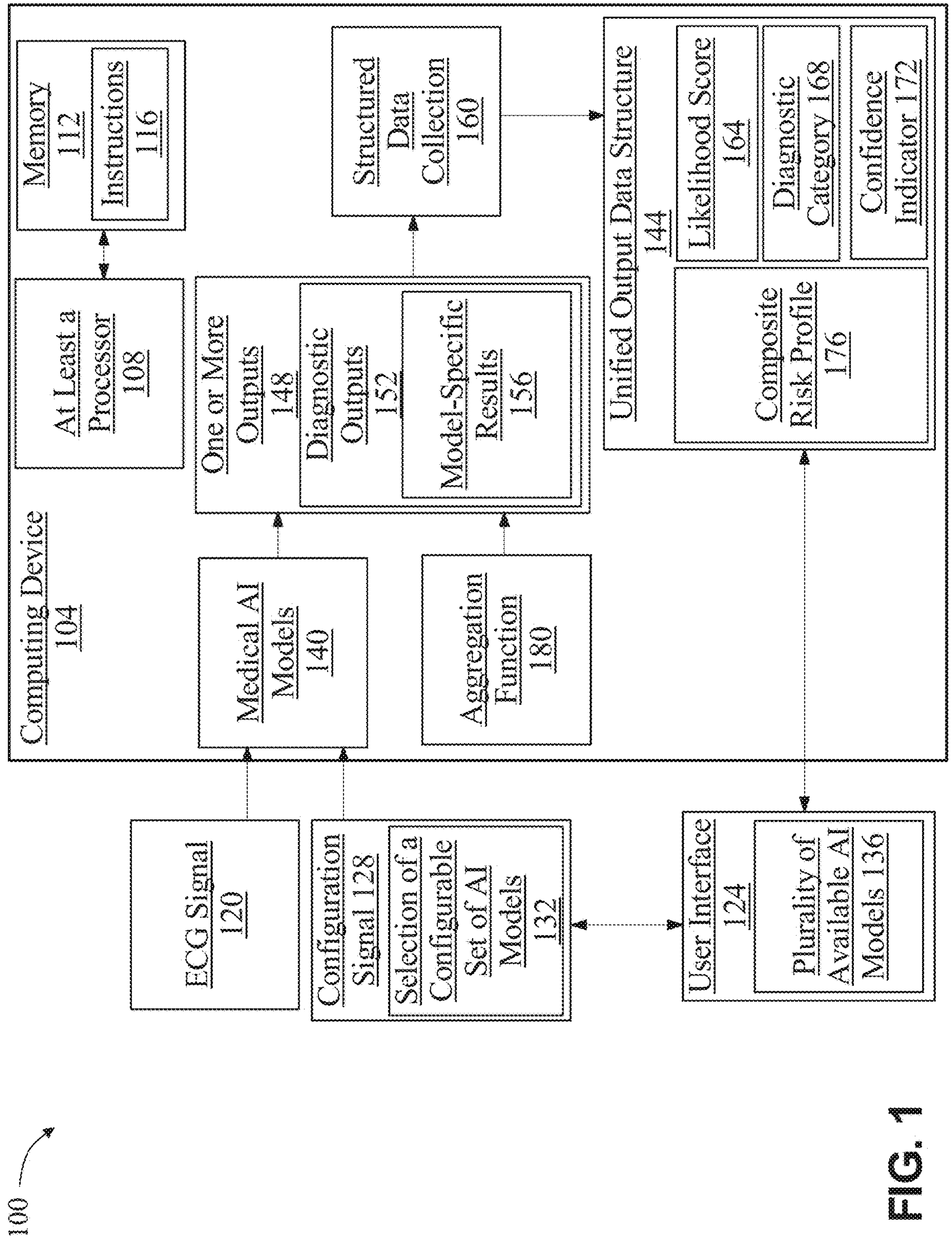
FIG. 1 is a block diagram illustrating an exemplary system for generating diagnostic information as a function of an ECG signal.

Referring now to FIG. 1, an exemplary embodiment of system 100 for generating diagnostic information as a function of an electrocardiogram (ECG) signal is illustrated. System 100 may include a circuitry such as without limitation at least a processor 108 communicatively connected to memory 112, wherein memory 112 contains instructions 116 configuring at least a processor 108 to perform one or more tasks as described herein; for instance, circuitry may include and/or be included in a computing device. As used in this disclosure, "communicatively connected" means connected by way of a connection, attachment, or linkage between two or more relata such as without limitation electronic components, modules, and/or devices which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals there between may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory may include a primary memory and a secondary memory. "Primary memory" also known as "random access memory" (RAM) for the purposes of this disclosure is a short-term storage device in which information is processed. In one or more embodiments, during use of the computing device, instructions and/or information may be transmitted to primary memory wherein information may be processed. In one or more embodiments, information may only be populated within primary memory while a particular software is running. In one or more embodiments, information within primary memory is wiped and/or removed after the computing device has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor. In one or more embodiments, data is transferred from secondary to primary memory wherein circuitry may access the information from primary memory.

Circuitry may alternatively or additionally be implemented by configuring a hardware device such as a combinatorial or sequential logic circuit, an application-specific integrated circuit (ASIC), a field-programmable gate array (FPGA), or other hardware unit; memory may be attached thereto to further configure the hardware unit using read-only memory (ROM) or any other static or writable memory as described in this disclosure. Alternatively or additionally, hardware units and/or modules may be combined with and/or in communication with a processor, such as without limitation in a system-on-chip architecture wherein some functions are configured by modification or design of hardware circuitry, such as without limitation FPGA circuitry, while others are configured in the form of instructions in memory for one or more processors. As a non-limiting example, any step or combination of steps described herein may be performed entirely using hardware circuit configured to perform such steps either with static memory or rewritable memory. Such steps or combinations of steps may include signing with a digital signature, cryptographically hashing, evaluation of zero-knowledge proofs, or any other specific process described in this disclosure.

Further referring to FIG. 1, computing device 104 may include any computing device as described in this disclosure, including without limitation a microcontroller, microprocessor, digital signal processor (DSP) and/or system on a chip (SoC) as described in this disclosure. computing device 104 may include, be included in, and/or communicate with a mobile device such as a mobile telephone or smartphone. computing device 104 may include a single computing device operating independently, or may include two or more computing device operating in concert, in parallel, sequentially or the like; two or more computing devices may be included together in a single computing device or in two or more computing devices. computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. computing device 104 may distribute one or more computing tasks as described below across a plurality of computing devices of computing device, which may operate in parallel, in series, redundantly, or in any other manner used for distribution of tasks or memory between computing devices. computing device 104 may be implemented, as a non-limiting example, using a "shared nothing" architecture.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, in an embodiment, at least a processor 108 is configured to receive an ECG signal 120. For purposes of this disclosure, an "ECG signal" is a time-series representation of the electrical activity of a subject's heart. An ECG signal 120 may be captured using electrodes placed on the body. For example, the ECG signal 120 may include data from a standard 12-lead clinical ECG system, a reduced-lead system, such as 6-lead or 3-lead ambulatory monitors, or single-lead configurations, such as those generated by wearable devices, smartwatches, patch sensors, or handheld monitors. In an embodiment, the ECG signal 120 may be acquired in real time from an external device communicatively connected to system 100, such as an ECG acquisition module, patient monitoring device, or wearable sensor. Alternatively, the ECG signal 120 may be received as a stored digital record retrieved from an electronic health record (EHR) system, local storage device, network-connected repository, or cloud-based platform. This may include embodiments in which the ECG signal 120 is retrieved from a patient profile associated with the subject. For purposes of this disclosure, a "patient profile" is an electronic configuration associated with a subject that includes one or more stored medical records and associated metadata indicative of the subject's medical history. A patient profile may contain stored ECG signals from previous clinical encounters, laboratory test results, medication lists, prior diagnoses, demographic information (such as age, sex, height, and weight), imaging results (such as echocardiograms or chest radiographs), and other physiological or biometric data. In certain embodiments, each stored record in the patient profile may be associated with metadata including acquisition timestamps, device identifiers, clinical setting descriptors (e.g., inpatient, outpatient, emergency), and parameters related to data quality or completeness. In an embodiment, system 100 may utilize information contained within the patient profile to inform one or more downstream processes, such as selecting appropriate artificial intelligence (AI) models, generating default model configurations, modifying processing parameters, or contextualizing diagnostic outputs 152. In some embodiments, the patient profile may also include historical treatment outcomes or physician annotations, which may further guide system 100 behavior or output interpretation.

In continued reference to FIG. 1, in an embodiment, the ECG signal 120 may be formatted in a variety of digital representations, including but not limited to: raw voltage-over-time data arrays, compressed data formats (e.g., DICOM-ECG, SCP-ECG, or FDA HL7 aECG formats), or proprietary device-specific structures. In certain embodiments, at least a processor 108 may include one or more preprocessing modules configured to standardize incoming ECG signals into a uniform internal format suitable for analysis, including resampling, filtering, or lead mapping operations as necessary.

In further reference to FIG. 1, in an embodiment, at least a processor 108 is configured to receive, using a user interface 124, a configuration signal 128. For purposes of this disclosure, a "user interface" is a component configured to facilitate user interaction with one or more operational functions of a system. In certain embodiments, the user interface 124 may include a graphical user interface (GUI) displayed on a monitor, touchscreen, tablet, or handheld device. The GUI may present selectable options for configuring the set of AI models to be executed, including visual elements such as tabs, dropdown menus, checkboxes, toggle switches, or categorized panels grouping AI models by disease category. For purposes of this disclosure, an "AI model" is a machine-learning-based computational framework trained to identify patterns, classify inputs, or generate predictions from data. In some embodiments, an AI model may include, but is not limited to, neural networks (e.g., convolutional neural networks, recurrent neural networks), decision trees, support vector machines, or ensemble methods trained on labeled or unlabeled datasets. Each AI model may be configured to output diagnostic classifications, severity assessments, confidence scores, or other clinically relevant predictions based on features derived from the ECG signal and, optionally, supplemental metadata such as patient demographics or clinical history. In some embodiments, the user interface 124 may include fields or menus allowing the user to upload or associate patient-specific information, such as selecting a patient profile, entering demographic data, or specifying clinical context. In an embodiment, the user interface 124 may include command-line interfaces (CLI), voice-controlled systems, or application programming interfaces (API) configured for programmatic integration with external clinical systems, such as electronic health record (EHR) platforms or decision support tools. In some embodiments, the user interface 124 may support user-specific access profiles or clinical roles, allowing system behavior or interface options to be adapted based on user permissions, specialty, or institutional workflow requirements. In certain embodiments, the user interface 124 may be implemented locally on a workstation physically co-located with the ECG acquisition device, or may be deployed remotely over a network connection, allowing users to access system 100 using secure web-based portals or mobile applications. Remote access may be implemented using encrypted communication protocols to ensure security and compliance with applicable data protection regulations, such as HIPAA or GDPR where applicable. In some examples, the user interface 124 may be accessed through a browser-based platform hosted on a cloud server, or via a dedicated application installed on a mobile device or clinical workstation.

Still referring to FIG. 1, in an embodiment, the user interface 124 may be configured to display a plurality of selectable AI models grouped under disease category labels. Each disease category label may correspond to a group of AI models associated with detection or prediction of related disease conditions. For example, a "Cardiac Dysfunction" category may include models for detecting left ventricular systolic dysfunction, heart failure with preserved ejection fraction, and arrhythmia risk, while a "Pulmonary Disease" category may group models relating to pulmonary hypertension or chronic obstructive pulmonary disease (COPD) detection. In some embodiments, the user interface 124 may present the disease categories as graphical tabs, panels, or collapsible menus, allowing the user to navigate among categories and select one or more AI models to be included in the configurable set. This arrangement may facilitate efficient model selection, reduce user cognitive load, and allow dynamic tailoring of the diagnostic panel based on patient-specific needs or clinical priorities.

In further reference to FIG. 1, for purposes of this disclosure, a "configuration signal" is a signal generated through the user interface 124 that instructs the system to prepare a specific configuration of one or more processing components. In an embodiment, the configuration signal 128 may include a selection of a configurable set of AI models 132, wherein the configurable set of AI models is selected from a plurality of available AI models 136 configured to perform disease-specific detection. For purposes of this disclosure, disease-specific detection refers to the use of AI models trained to identify patterns in ECG signals that are indicative of particular medical conditions or diagnostic categories, such as atrial fibrillation, reduced ejection fraction, or pulmonary hypertension. Each model may be optimized to detect features associated with a specific disease state, allowing the system to tailor diagnostic analysis to patient-specific risks or clinical contexts. The configuration signal 128 may be generated, for example, based on user input received through the user interface 124, such as selecting one or more models grouped under disease category labels. In some embodiments, the configuration signal 128 may include additional parameters, such as model execution priorities, resource constraints (e.g., processing time limits or hardware availability), or patient-specific contextual information that may inform downstream processing. The configuration signal 128 may be represented as a structured data object (e.g., a JSON, XML, or protocol buffer object), a serialized message, or another internal data format compatible with system's 100 architecture. In certain embodiments, the configuration signal 128 may be stored as a named configuration or version-controlled object, enabling reuse, auditability, or retrospective analysis of executed diagnostic workflows. This may facilitate clinical documentation requirements, standardized diagnostic protocols, or continuity of care across clinical sessions.

With further reference to FIG. 1, in an embodiment, the configurable set of AI models may include at least one model configured to detect a presence of a disease and at least one model configured to predict a severity of the disease. For purposes of this disclosure, a model configured to detect the presence of a disease refers to an AI model that has been trained to output a prediction indicating whether a given condition is likely present based on features derived from the ECG signal 120. For example, such a model may be configured to classify whether the ECG signal 120 exhibits features consistent with reduced left ventricular ejection fraction, atrial fibrillation, or conduction abnormalities. In contrast, a model configured to predict severity may have been trained to provide a graded output indicative of the extent or progression of a detected condition. For instance, in the case of reduced ejection fraction, a severity model may distinguish between mild, moderate, and severe dysfunction based on quantitative thresholds or risk stratification criteria. In some embodiments, severity prediction models may operate as follow-up processes triggered by a positive finding from a corresponding disease detection model or may operate concurrently on the same ECG signal 120. The configurable set of AI models may therefore include combinations of detection and severity models, allowing the system to generate diagnostic outputs 152 that provide both binary classification (e.g., presence/absence) and stratified insights (e.g., disease stage or urgency level). In an embodiment, system 100 may organize outputs from detection and severity models in the unified output data structure 144 using associated metadata, such as model type, disease target, and severity scale, to facilitate review by the end user.

In continued reference to FIG. 1, in an embodiment, at least one AI model of the configurable set of AI models has been trained on a disease-specific training dataset. In an embodiment, the disease-specific training dataset may include a dataset that includes ECG signals and, in some embodiments, additional contextual information associated with a specific target condition or disease domain. The dataset may include labeled data, such as ECG recordings paired with diagnostic annotations or clinical outcomes and/or may include unlabeled data used in self-supervised, unsupervised, or contrastive learning approaches. The disease-specific dataset may be disease-specific, meaning that it is designed to teach the AI models to recognize patterns of disease-related changes in ECG signals rather than to model individual patient characteristics. For instance, a dataset for heart failure detection may contain ECG signals from a broad range of patients with heart failure but does not include patient-specific identifiers. The model may be trained to recognize patterns such as altered QRS morphology, ST-segment changes, or heart rate variability, which are indicative of heart failure. In some embodiments, demographic and clinical information (e.g., age, sex, comorbidities) may be included as features within the training data, but they may not be the focus of the model's primary learning objective. Rather, this information may serve to inform the model's predictions by improving generalization or performance across population subgroups, while maintaining the model's primary optimization objective of detecting disease-related ECG signal 120 features. For example, an AI model trained to detect atrial fibrillation might use age as an additional factor, since the prevalence of AFib increases with age, but the model is ultimately focused on detecting the unique electrical pattern associated with AFib. In an embodiment, the disease-specific training dataset may be derived from a single institution or aggregated from multiple clinical sources, and may include a combination of historical ECGs, synthetically generated signals, or augmented signals reflecting variation in lead configurations or signal quality. Training using disease-specific datasets may enable models to learn patterns that are diagnostically relevant to particular conditions, such as atrial fibrillation, heart failure, myocardial ischemia, or conduction system disorders. Different models within the plurality of available AI models 136 may each be trained on separate disease-specific datasets to optimize performance for their respective diagnostic tasks.

Still referring to FIG. 1, in an embodiment, the configurable set of AI models may include two or more linked models, wherein a result generated by a first model is used to trigger execution of a second model. For purposes of this disclosure, "linked models" refers to two or more AI models that are configured such that the execution of one model, or the result produced by that model, governs or influences the activation or selection of another model. The linkage may be predefined using conditional logic, such as if-then rules; threshold-based criteria, such as executing a downstream model only if the confidence score of an upstream model exceeds a predefined threshold; or rule-based associations derived from known co-occurrence patterns between diagnostic targets. In some embodiments, linkage may be based on learned dependencies, wherein the system includes a model orchestration layer or control module that has been trained to determine execution sequences based on features extracted from the input signal, prior model outputs, or contextual metadata associated with the patient or signal acquisition event. The orchestration layer may apply decision logic dynamically, enabling flexible diagnostic workflows that evolve based on real-time system inputs or intermediate results. For example, a model configured to detect the presence of reduced ejection fraction may, upon a positive result, trigger execution of a downstream model configured to assess the likely severity of dysfunction or predict clinical decompensation risk. In other embodiments, a model that detects atrial fibrillation may prompt a second model that estimates thromboembolic risk or recommends a need for anticoagulation assessment. In an embodiment, linkages between models may be static, such that certain diagnostic pathways are always followed under specific conditions, or dynamic, where real-time patient data or model confidence levels influence which additional models are executed. This architecture may allow system 100 to implement intelligent execution pathways that optimize computational efficiency while delivering progressively refined diagnostic outputs 152 when warranted by earlier results.

In further reference to FIG. 1, in an embodiment, the plurality of available AI models 136 and training processes thereof may align with the models and training methodologies as described in the following U.S. patent applications: U.S. patent application Ser. No. 18/750,336, filed on Jun. 21, 2024, entitled "SYSTEMS AND METHODS FOR TRACKING CARDIAC VALUES," U.S. patent application Ser. No. 18/771,914, filed on Jul. 12, 2024, entitled "APPARATUS AND METHODS FOR IDENTIFYING ABNORMAL BIOMEDICAL FEATURES WITHIN IMAGE OF BIOMEDICAL DATA," U.S. patent application Ser. No. 18/771,678, filed on Jul. 12, 2024, entitled "APPARATUS AND METHOD FOR DETECTING HYPERTENSION ATTRIBUTES," U.S. patent application Ser. No. 18/771,472, filed on Jul. 12, 2024, entitled "APPARATUS AND A METHOD FOR IDENTIFYING THE PROGRESSION OF CORONARY HEART DISEASE," U.S. patent application Ser. No. 18/773,302, filed on Jul. 15, 2024, entitled "APPARATUS AND METHOD FOR DETERMINING WOMENS HEALTH ATTRIBUTES IN FEMALE CLASSIFICATION TIME-SERIES DATA," U.S. patent application Ser. No. 18/773,195, filed on Jul. 15, 2024, entitled "APPARATUS AND METHOD FOR GENERATING A PREOPERATIVE DATA STRUCTURE USING A PRE-OPERATIVE PANEL," each of which are incorporated herein by reference in their entirety. These applications provide exemplary embodiments of disease-specific model architectures, training workflows, data labeling schemas, and clinical classification strategies that may be used by or integrated into the plurality of available AI models 136 described herein. In the event of any inconsistency, the present disclosure shall control.

With continued reference to FIG. 1, in an embodiment, at least a processor 108 may be further configured to, in response to the configuration signal 128, prompt a user to additionally select one or more related AI models as a function of a predefined association between the selection of a configurable set of AI models 132 and other models within the plurality of available AI models 136. For purposes of this disclosure, a "prompt" is a generated signal, message, or visual interface element presented using the user interface 124. In some embodiments, the prompt may be presented as a contextual overlay, a pop-up panel, an inline expansion of a selected model group, or a "suggested models" list that updates dynamically as the user interacts with the user interface 124. The content and ordering of the prompt may reflect one or more relevance scores, priority flags, or usage patterns derived from a model relationship database or configuration mapping table.

In further reference to FIG. 1, in an embodiment, these predefined associations may be stored in a model relationship database or configuration mapping table that links models based on shared disease domains, complementary diagnostic functions, known temporal or causal progressions of clinical events, or frequently co-occurring diagnostic categories. For example, selection of an AI model associated with myocardial infarction detection may prompt the user to also consider models related to arrhythmia risk, left ventricular ejection fraction (LVEF) classification, or stress cardiomyopathy, depending on which other models are already selected, or which disease categories are currently active in the interface. Similarly, selection of a model targeting chronic obstructive pulmonary disease (COPD) may be associated with prompts to consider pulmonary hypertension or right heart strain models. The predefined associations may take several forms, including but not limited to: (i) static one-to-one or one-to-many mappings, wherein a given model is linked to a fixed set of complementary models; (ii) hierarchical taxonomies, where models are grouped under broader diagnostic categories, such as "Cardiovascular," "Pulmonary," or "Metabolic," and associations are inferred based on shared group membership; (iii) pathway-based associations, reflecting curated diagnostic sequences or evaluation protocols (e.g., ischemia detection followed by infarction confirmation and risk stratification); (iv) confidence-weighted or threshold-driven links, wherein a model's output triggers recommendations for follow-up models only if its confidence or risk score exceeds a predefined value; and (v) usage-based associations, wherein associations are learned or updated based on historical co-selection patterns, institutional usage logs, or user-level preferences. In an embodiment, the model relationship database may include metadata structures for storing the type of association (e.g., static, learned), the strength or weight of the association (e.g., relevance score or frequency count), context flags (e.g., outpatient, emergency), and any override rules (e.g., suppress prompt if the model is already selected). These configurations may be curated manually or updated dynamically based on institutional guidelines, structured knowledge sources, or post-deployment learning from aggregate system behavior.

With further reference to FIG. 1, in an embodiment, upon receiving a configuration signal 128, the prompting system may query the model relationship database using the selected model identifier(s) to retrieve associated model suggestions. These suggestions may be displayed in a dedicated prompt area of the user interface 124, visually distinguished from manually selected models. In some embodiments, suggestions may include justifications or tags (e.g., "commonly co-selected," "recommended for risk staging," "complements selected model"), and may support one-click inclusion into the configurable set. This prompting functionality may enable users to construct diagnostic panels that are broader, more contextually relevant, and more efficient to configure. Further, it may reduce reliance on user memory or manual navigation of large model libraries, improve completeness of evaluation in multi-system or comorbid conditions, and may help enforce diagnostic consistency, streamline workflows, and support downstream documentation and billing processes. In some embodiments, system 100 may maintain a diagnostic panel log recording the initial configuration, user selections, suggested models, execution outcomes, and any subsequent modifications, enabling traceability, quality assurance, and retrospective review.

In continued reference to FIG. 1, in an embodiment, at least a processor 108 may be further configured to generate a default configuration of the configurable set of AI models as a function of one or more patient-specific characteristics. For purposes of this disclosure, a "default configuration" is an automatically generated, initial selection of one or more artificial intelligence models from the plurality of available AI models 136, produced by system 100 prior to or in the absence of user selection. In an embodiment, the default configuration may be dynamically generated in response to receipt of patient-specific information or may be based on predefined mappings established during system deployment or training. The default configuration may be designed to present a user with a contextually appropriate subset of models, thereby reducing configuration effort, minimizing selection errors, and increasing consistency across clinical workflows. For purposes of this disclosure, a "patient-specific characteristic" is a data element associated with a particular subject that may inform the relevance, utility, or prioritization of one or more AI models. Such characteristics may include but are not limited to demographic data (e.g., age, sex, weight, height), medical history (e.g., prior diagnoses, chronic conditions, recent procedures); current clinical data (e.g., active medications, presenting symptoms), and prior physiological signals or derived metrics (e.g., historical ECG findings, previously generated diagnostic outputs 152). Patient-specific characteristics may be retrieved from a patient profile, imported from an electronic health record system, or entered manually using the user interface 124.

In further reference to FIG. 1, in an embodiment, generating a default configuration may include identifying one or more disease categories associated with the patient-specific characteristics. For instance, a patient with a documented history of hypertension and left ventricular hypertrophy may be mapped to disease categories such as heart failure risk, left-sided conduction abnormality, and arrhythmia detection. This mapping may be performed by a rule-based engine, a disease-category classifier, or a trained machine-learning model that outputs one or more relevant categories given an input set of patient characteristics. Once one or more disease categories are identified, system 100 may generate the default configuration by selecting AI models associated with those categories from the broader model library. For example, identifying the "Cardiac Dysfunction" category may trigger selection of models for detecting systolic dysfunction, classifying ejection fraction severity, and estimating hospitalization risk. The default configuration may be presented to the user in the user interface 124 as a prechecked set of models within the disease category groupings, while still allowing for user override or refinement. This functionality may be useful in scenarios where rapid model selection is required, such as in time-sensitive or high-throughput environments, or when users are unfamiliar with the full catalog of available models. By leveraging patient-specific inputs to preconfigure the diagnostic panel, system 100 can reduce cognitive load, improve user satisfaction, and ensure that high-value models are not inadvertently omitted. In some embodiments, system 100 may also log user modifications to the default configuration over time, enabling adaptive refinement of the default generation logic based on observed user preferences or outcomes.

With continued reference to FIG. 1, in an embodiment, system 100 may include an orchestration layer configured to manage the execution flow of the configurable set of AI models based on one or more execution policies, model dependencies, or contextual signals. As used herein, the "orchestration layer" is a software-implemented control module or coordinating subsystem that governs when and how each AI model within the system is activated. The orchestration layer may receive the configuration signal 128 and determine which AI models are to be executed, and in what order, based on predefined model linkages, real-time system inputs, patient-specific metadata, or prior model outputs. In some embodiments, the orchestration layer may apply static execution rules defined by developers or administrators, such as always executing a severity model after a positive detection result. In other embodiments, the orchestration layer may incorporate a learned execution strategy, wherein a machine-learning model has been trained to optimize model sequencing based on historical system behavior, model performance metrics, or known co-occurrence patterns between diagnostic outcomes. The orchestration layer may also be responsible for allocating computational resources, queuing model runs, suppressing redundant executions, or prioritizing high-utility models in bandwidth-constrained environments. Outputs from the orchestration layer may include a model execution schedule, a dynamically updated list of selected models, or intermediate trigger signals that initiate downstream model execution. In some embodiments, the orchestration layer may update execution policies dynamically based on partial outputs, patient risk indicators, or elapsed processing time, allowing system 100 to adjust or re-prioritize model execution in real time. This adaptive behavior may be particularly useful in emergencies or time-constrained diagnostic environments. In an embodiment, the orchestration layer may operate locally within the medical AI module 140, or as a distinct logical component accessible through a system-wide control interface.

With continued reference to FIG. 1, in an embodiment, at least a processor 108 is configured to configure a medical AI module 140 as a function of the configuration signal 128. For purposes of this disclosure, a "medical AI module" refers to a software component comprising one or more artificial intelligence models, model execution engines, and supporting software routines configured to perform diagnostic, predictive, or stratification analyses on electrocardiogram (ECG) signals. In an embodiment, the medical AI module 140 may be implemented as a standalone software component, a containerized service, or an integrated subcomponent of system 100, and may include hardware acceleration support where applicable, for example, using GPUs or specialized inference processors. In an embodiment, configuring the medical AI module 140 may include selecting, loading, or activating a subset of AI models from the plurality of available models, as specified by the configuration signal 128. The configuration may further include initializing model-specific parameters, loading reference datasets or normalization baselines, and applying resource allocation settings, such as prioritizing certain models in accordance with system constraints or urgency indicators. Configuration may also include preparing the ECG signal 120 for model input, such as applying preprocessing routines (e.g., lead alignment, signal filtering, or normalization) required by one or more models. In certain embodiments, configuring the medical AI module 140 may include establishing the model execution order and associated dependencies, as defined by linked model logic or orchestration layer rules. For example, if the configuration signal 128 identifies a linked sequence of models for detection and severity assessment, the medical AI module 140 may be configured to execute these models in a pipelined fashion, passing intermediate outputs where necessary.

In continued reference to FIG. 1, in an embodiment, configuring the medical AI module 140 may include analyzing the ECG signal 120 using the selection of the configurable set of artificial intelligence models. Each model may process the ECG signal 120 independently or in combination with auxiliary inputs, such as patient-specific metadata or model-specific parameters, to generate diagnostic outputs 152. The results of this analysis may be encapsulated into a structured data object, such as a unified output data structure 144, for subsequent review, visualization, or clinical decision support. In some embodiments, the medical AI module 140 may also produce confidence scores, output tags, or traceability metadata, supporting downstream auditing and interpretability.

With further reference to FIG. 1, in some embodiments, system 100 may be further configured to interface with an external clinical decision orchestration platform, such as one configured to process condition-specific diagnostic inputs and recommend next-best clinical actions based on institutional protocols or patient-specific factors. For example, once the unified output data structure 144 is generated, system 100 may transmit the relevant diagnostic outputs, likelihood scores, and composite risk indicators to an external ordering engine configured to evaluate and triage findings across diagnostic domains. This external engine may use rule-based logic, predictive models, or clinician-defined prioritization schemas to determine appropriate downstream interventions or care coordination steps. In this way, ECG-based AI outputs generated by system 100 can be contextualized and integrated into broader workflows such as imaging recommendations, subspecialty referrals, or automated population health alerts. In some configurations, the external system may also influence upstream behavior by modifying or preconfiguring the AI model panel presented to the user, for example, by suggesting cardiac or pulmonary models based on prior clinical data or structured orders. This bidirectional interface may enable a cohesive, context-aware pipeline from ECG acquisition to clinical action, supporting scalable adoption of AI-driven diagnostics within routine care pathways.

In further reference to FIG. 1, in an embodiment, at least a processor 108 is configured to generate a unified output data structure 144 as a function of one or more outputs 148 generated by the configurable set of AI models. For purposes of this disclosure, a "unified output data structure" is a structured, machine-readable data object or collection that consolidates the results produced by the execution of multiple artificial intelligence models. In an embodiment, the unified output data structure 144 may be efficiently interpreted, presented to the user, stored for record-keeping, or transmitted to external systems. For example, the unified output data structure 144 may be implemented as a structured document (e.g., JSON, XML, or protocol buffer format), a database object, or a memory-resident data array, depending on system configuration. In an embodiment, generating a unified output data structure 144 may include receiving diagnostic outputs 152 generated by each AI model of the configurable set of AI models, each diagnostic output including a model-specific result 156. For purposes of this disclosure, a "diagnostic output" is a machine-generated output produced by an artificial intelligence model in response to analysis of an input ECG signal 120. Each diagnostic output may include a primary prediction or classification, one or more auxiliary indicators, and metadata that supports clinical interpretation, provenance tracking, or system integration. Each output may also be accompanied by auxiliary information, such as a confidence score, model version identifier, timestamp of execution, and an internal model identifier or tag corresponding to the disease category or detection target. In an embodiment, each diagnostic output may include a model-specific result 156. A "model-specific result," for purposes of this disclosure, is the specific prediction or classification produced by an individual AI model within the configurable set of AI models. The model-specific result 156 may take various forms depending on the model type and training objective. For example, the result may include a binary classification indicating the likely presence or absence of a disease condition, a probabilistic score representing the model's confidence in a given classification, a multi-class severity label indicating disease stage or risk level (such as mild, moderate, or severe), or a recommendation flag corresponding to a follow-up diagnostic or therapeutic action. Each diagnostic output may further include associated metadata, such as a confidence score, a model identifier (e.g., name or version number), a timestamp indicating when the result was generated, and a categorical label indicating the disease type or clinical domain addressed by the model. The metadata may also include contextual variables, such as whether the model was triggered automatically or by user selection, or whether it was part of a linked model sequence.

With continued reference to FIG. 1, in some embodiments, generating the unified output data structure 144 may include standardizing each diagnostic output into a common schema or template. For example, each output may be transformed into a structured representation including: (i) an identifier for the diagnostic target (e.g., condition being evaluated), (ii) the output value or prediction generated by the model, (iii) the confidence or probability associated with the prediction, (iv) any severity or risk stratification label, (v) information identifying the model that produced the result, and/or (vi) execution context data such as the model's runtime parameters or operating environment. The use of a standardized output format may allow downstream components, such as a user interface 124, orchestration layer, or audit log processor, to process and interpret the results in a consistent and predictable manner.

With continued reference to FIG. 1, in an embodiment, generating a unified output data structure 144 may include organizing the processed diagnostic outputs 152 into a structured data collection 160. For purposes of this disclosure, a "structured data collection" refers to an organized, machine-readable compilation of diagnostic outputs in which each entry adheres to a predefined schema or format that enables systematic parsing, analysis, and interoperability. For example, a structured data collection 160 may include a sequential list, a disease-category hierarchy, or a diagnostic map indexed by risk domain or model linkage relationships. This structured collection may be designed to optimize for latency in rendering, user navigation, or compatibility with external systems, including electronic health record (EHR) platforms or clinical decision support tools. In some embodiments, the unified output data structure 144 may also include interpretability metadata or traceability elements. These may identify key ECG signal 120 features that contributed most strongly to the model's output, or record intermediate results used by linked models, thereby supporting transparency, explainability, and downstream auditing or clinical review. This unified output approach may enable system 100 to consolidate the results from multiple AI models, each potentially trained using different datasets, optimized for different disease conditions, or configured with different thresholds, into a coherent and standardized report format suitable for presentation, review, or integration into clinical workflows.

In continued reference to FIG. 1, in an embodiment, at least a processor 108 may be further configured to display at the user interface 124, for each diagnostic output, a likelihood score 164, a diagnostic category 168, and a confidence indicator 172 associated with an AI model result. For purposes of this disclosure, a "likelihood score" is a quantitative value representing the model's estimate that a particular condition is present or will develop, based on the analyzed ECG signal 120. For example, the quantitative value may include, without limitation a probability, risk index, or percentage. A "diagnostic category," for purposes of this disclosure, is a label identifying the clinical condition or disease domain associated with the model's output. For example, a diagnosis category may include atrial fibrillation, heart failure, or pulmonary hypertension. This label may be displayed as plain text, iconographic shorthand, or color-coded indicators, depending on the interface implementation. A "confidence indicator," for purposes of this disclosure, is additional context about the reliability or stability of the AI model's prediction. In some embodiments, the confidence indicator 172 may be displayed as a numeric confidence interval, a visual gauge or icon (e.g., low/medium/high confidence), or a graphical overlay such as a confidence bar or opacity effect. The user interface 124 may be further configured to group outputs by category, display them in a prioritized or severity-weighted order, and/or allow filtering or sorting based on any of these attributes.

With further reference to FIG. 1, in an embodiment, the user interface 124 may be configured to render the likelihood score 164, diagnostic category 168, and confidence indicator 172 in an interactive display panel associated with each diagnostic output. Each panel may correspond to a result from an individual AI model and may be presented within a scrollable or expandable interface area grouped by disease domain or risk severity. In an embodiment, the likelihood score 164 may be displayed as a numeric percentage or score value, optionally accompanied by a colored progress bar or ring to visually represent magnitude. For example, a model-specific result 156 predicting atrial fibrillation with a 92% likelihood may display both the numeric value and a nearly full-colored arc to reinforce the model's output visually. The diagnostic category 168 may be displayed as a static or dynamically styled label, such as a header above the result panel or a tag attached to the model-specific result 156. In some embodiments, diagnostic categories may be color-coded by organ system or disease severity, enabling quick visual parsing across multiple outputs. Iconography or abbreviation schemes may also be used for space-constrained views (e.g., mobile interfaces). In an embodiment, the confidence indicator 172 may be positioned adjacent to the likelihood score 164 and may be expressed using one or more display modes, such as: (i) a confidence interval range presented as a bracketed numeric span (e.g., 85-95%), (ii) a visual indicator (e.g., three-tier scale: low, medium, high), or (iii) a dynamic display feature, such as adjusting the opacity or sharpness of the output panel to reflect varying levels of prediction certainty. In some embodiments, a tooltip or detail-expansion function may allow the user to view additional metadata associated with the confidence indicator 172, including model performance metrics, training data notes, or explanation artifacts. In further embodiments, user interaction data and post-diagnostic outcomes may be used as feedback inputs to adaptively refine the model selection interface, default configurations, or future AI model deployments. For instance, if a particular diagnostic output consistently results in high user confidence ratings and clinically validated follow-up outcomes, its prominence or default inclusion in similar patient cohorts may be increased. Conversely, models receiving consistent overrides, low confidence ratings, or limited correlation to actionable outcomes may be deprioritized or flagged for review. This clinician-in-the-loop learning approach may allow system 100 to evolve dynamically in response to real-world usage and outcomes, while preserving a traceable record of system changes and rationale.

With continued reference to FIG. 1, in an embodiment, the user interface 124 may further be configured to automatically update these visual elements in real time or near real time as the medical AI module 140 generates or modifies outputs. For example, as the configurable set of AI models completes execution, the user interface 124 may incrementally populate each output panel with new results, dynamically adjusting display order based on predefined rules such as severity prioritization, confidence thresholds, or time-toexecution. In embodiments supporting linked models or adaptive workflows, the user interface 124 may also update visual indicators in response to intermediate results, such as activating a new output panel when a downstream model is triggered based on a prior finding. This dynamic presentation of diagnostic output elements may enable the user to rapidly interpret the results of multiple AI models, identify high-risk findings, and trace the model lineage and confidence associated with each prediction, thereby supporting timely and transparent clinical decision-making.

In further reference to FIG. 1, in an embodiment, the user interface 124 may further be configured to support filtering, sorting, and navigation across diagnostic outputs 152 based on one or more output attributes. For example, users may apply filters to display only diagnostic outputs 152 exceeding a minimum likelihood score 164, falling within a particular confidence range, or associated with selected diagnostic categories such as cardiac, pulmonary, or metabolic conditions. Filtering controls may include toggle switches, multi-select dropdowns, range sliders, or search fields allowing entry of keywords or model identifiers. In some embodiments, the user interface 124 may support severity-based sorting, wherein the most urgent or highest-risk outputs are pinned or promoted to the top of the results panel. Alternatively, results may be grouped by organ system, model type (e.g., detection vs. severity), or execution order based on linked model sequences. The user interface 124 may also include expandable panels or collapsible sections that allow users to drill down into specific model results while maintaining a compact, navigable overview. To further assist user interaction, system 100 may display status indicators or loading animations for outputs that are still being computed by the medical AI module 140 and may highlight newly available results as they appear. In some embodiments, output panels may include interactive elements such as "expand for details," "view explanation," or "compare with prior controls," which may reveal model rationales, contributing signal features, or historical outputs from the same model applied to earlier ECGs. The combination of real-time updates and flexible navigation tools may enable clinicians to efficiently focus on the most clinically relevant results, customize their view to specific diagnostic contexts, and interact with model outputs in a transparent and traceable manner.

Still referring to FIG. 1, in an embodiment, each diagnostic output displayed at the user interface 124 may include an explanation layer configured to provide interpretability features that assist users in understanding the basis of a model's result. The explanation layer may be accessible through an interactive control such as an expandable section, tooltip, or "view explanation" button associated with each model output panel. When activated, the explanation layer may reveal one or more key features of the input ECG signal 120 that most significantly influenced the model's prediction, such as elevated heart rate variability, abnormal QRS morphology, or irregular P-wave intervals. In some embodiments, the explanation layer may be generated using a surrogate model or attribution method trained or configured to correlate specific ECG parameters with model outputs. Examples of suitable techniques may include Shapley value approximations, feature importance rankings, gradient-based saliency maps, or regression-based surrogate models trained on model input-output pairs. The explanation may also indicate whether auxiliary features, such as age, sex, or comorbidities, contributed to the model's prediction or were present as neutral context. The user interface 124 may display explanations using textual summaries (e.g., "Irregular RR interval contributed to AFib prediction"), graphical overlays on waveform segments, heatmaps, or annotated lists of top-ranked features. In some embodiments, explanations may be color-coded to convey directionality (e.g., features increasing vs. decreasing the predicted likelihood), and may include confidence scores or contribution weights. This explanation layer may improve clinical trust, support diagnostic validation, and assist with documentation or reporting. Additionally, it may provide a basis for downstream quality assurance workflows, second-opinion reviews, or compliance with regulatory guidance concerning algorithmic transparency and fairness.

With continued reference to FIG. 1, in an embodiment, the user interface 124 may be further configured to receive and log user feedback related to the explanation layer associated with each diagnostic output. For example, system 100 may present interactive options allowing the user to rate the helpfulness of the explanation, flag inconsistencies, or submit annotations regarding clinical relevance. Feedback mechanisms may include binary controls (e.g., thumbs up/down), structured forms (e.g., "Was this explanation clear?"), or free-text fields for contextual comments. In some embodiments, this user feedback may be stored in a feedback log associated with the diagnostic session, model instance, or user profile. The feedback log may be used in offline analysis to assess explanation quality, detect systematic mismatches between user expectations and model behavior, or guide the retraining of surrogate explanation models. In other embodiments, feedback data may inform interface refinement, such as reordering feature contributions based on user preferences or simplifying explanation language over time. Where supported by institutional policy, aggregated feedback across multiple users or cases may be used to tune model selection logic, improve default configurations, or inform model deployment strategies. This clinician-in-the-loop functionality may enable system 100 to evolve its interpretability and user experience over time based on actual usage patterns and expert judgment, while preserving transparency and auditability for regulatory or research purposes.

In continued reference to FIG. 1, in an embodiment, at least a processor 108 may be configured to generate a composite risk profile 176 as part of the unified output data structure 144 by executing a structured aggregation process across the diagnostic outputs 152 of the configurable set of AI models. For purposes of this disclosure, a "composite risk profile" refers to a synthesized data object that reflects a subject's consolidated diagnostic risk state. The process of generating the composite risk profile 176 may begin by parsing each diagnostic output to extract relevant elements, including prediction values, confidence metrics, diagnostic category 168 labels, and model identifiers. These extracted elements may be mapped into a normalized internal representation, such as a matrix or multidimensional feature vector, where each row corresponds to an AI model output and each column corresponds to a standardized parameter (e.g., disease type, likelihood score 164, severity label, or model confidence weight). Once this intermediate representation is established, system 100 may apply one or more aggregation functions 180 that operate over the set of diagnostic outputs 152 to compute composite indicators. These functions may include, for example, weighted summation of disease-specific likelihood scores 164 (with weights determined based on model confidence, patient relevance, or disease severity); rule-based thresholding (where a composite risk flag is raised if one or more outputs 148 exceed predefined cutoffs); hierarchical stratification (in which outputs are grouped and summarized by diagnostic domain); or application of a meta-model trained to assess aggregate risk from a vector of model-specific inputs. The resulting composite profile may be assembled into a structured data object comprising one or more of: a global risk score, a tiered severity classification, and a per-category summary of positive, negative, or indeterminate findings. The structured profile may additionally include metadata describing the aggregation process, such as the specific models used, whether outputs were excluded due to confidence thresholds, and the logic chain or model version associated with the profile.

In further reference to FIG. 1, in some embodiments, the composite risk profile 176 may be generated incrementally and updated in real time as new diagnostic outputs 152 are received. This may allow for early or progressive risk estimation, enabling system 100 to begin surfacing high-priority findings before the full panel of AI models has completed execution. To support clinical transparency and system auditability, the composite risk profile 176 may further include an embedded metadata layer that records the aggregation logic applied, output provenance, and any applied exclusion or weighting strategies. This traceability may be important for post-hoc review, quality control, or compliance with regulatory standards requiring explanation of AI-generated conclusions. Once generated, the composite risk profile 176 may be surfaced at the user interface 124 as a visual summary, such as a color-coded indicator, graphical dashboard element, or stratified panel view, that presents a consolidated representation of patient risk. The profile may also be configured for export or downstream integration into electronic health records, structured reports, billing systems, or population health registries.

With continued reference to FIG. 1, in an embodiment, at least a processor 108 is configured to output the unified output data structure 144. In an embodiment, outputting the unified output data structure 144 may include transmitting, rendering, storing, or making accessible the compiled set of diagnostic outputs 152, composite risk profile 176, if generated, and/or associated metadata produced by the medical AI module 140. In some embodiments, outputting may be initiated as an event-driven process, wherein partial outputs are transmitted as soon as they are available, allowing progressive rendering or early alerting while remaining models continue execution. The output may be directed to one or more downstream components within system 100 or transmitted to external systems or user interfaces 124 for review, storage, or action. In an embodiment, outputting the unified output data structure 144 may include rendering the unified output data structure 144 directly to a clinician-facing user interface 124, where the information may be parsed and displayed in structured panels, graphical summaries, or interactive result lists. At least a processor 108 may format the output using a structured encoding format such as JSON, XML, or HL7-compatible messages to facilitate interpretation by both human users and automated systems. In other embodiments, outputting may include transmitting the unified output data structure 144 to a network-connected destination, such as an electronic health record (EHR) system, clinical decision support system (CDSS), population health management platform, or institutional data warehouse.

In further reference to FIG. 1, the transmission may occur using secured protocols such as HTTPS, FHIR, or encrypted messaging APIs, and may include data validation or formatting steps required for conformance with interoperability standards. In an embodiment, system 100 may also be configured to log or persist the unified output data structure 144 in a local or cloud-based storage medium for audit, compliance, billing, research, or retrospective analysis. Outputting the unified output data structure 144 may further include versioning the result set, tagging each instance with metadata such as processing timestamp, AI model versions, user identifiers, or configuration signal 128 used to generate the results. In some embodiments, outputting the unified output data structure 144 may also involve triggering downstream workflows based on the contents of the structure. For example, high-risk results identified in the composite risk profile 176 may prompt automatic generation of alerts, enrollment in follow-up monitoring protocols, or activation of institutional triage queues. Outputting the unified output data structure 144 may therefore serve not only as a means of communicating information but also as an actionable step in a broader automated or semi-automated diagnostic pipeline. In an embodiment, the unified output data structure 144 may further include billing-support metadata, such as standardized diagnostic codes (e.g., ICD-10, CPT), timestamped confirmation of model execution, and clinician review indicators. This structured output may be formatted to support integration with billing documentation systems or compliance auditing tools, and may be stored or exported as part of a structured report suitable for reimbursement under medical billing guidelines covering AI-assisted diagnostic services.

With continued reference to FIG. 1, in some embodiments, system 100 may be further configured to log post-diagnostic clinical outcomes or follow-up actions taken in response to the generated diagnostic outputs 152. For example, system 100 may record whether the patient was referred for further testing, whether treatment was initiated, or whether adverse events occurred following the output of a high-risk diagnostic finding. This outcome-tracking functionality may be implemented using structured fields linked to electronic health record (EHR) events, manual user input, or integration with downstream care coordination systems. Logged outcomes may be associated with corresponding AI model results, timestamps, and configuration identifiers, thereby enabling longitudinal analysis of diagnostic efficacy, adherence to system-supported recommendations, and potential correlations with improved patient outcomes.

In continued reference to FIG. 1, in some embodiments, system 100 may be further configured to tailor the output of the unified output data structure 144 based on the role, permissions, or user profile of the recipient accessing the data. For purposes of this disclosure, a "role-specific output" refers to a filtered, reformatted, or reorganized view of the underlying diagnostic information designed to align with the responsibilities, expertise, and clinical workflow needs of a particular user type. For example, a nurse or allied health professional may be presented with a simplified summary view of key findings and risk alerts, highlighting only high-priority results or care-pathway triggers. In contrast, a specialist such as a cardiologist may receive the full set of model-specific outputs, confidence indicators 172, and explanation layers, allowing in-depth review and clinical validation. Administrative or billing personnel may be presented with outputs formatted for reimbursement coding or quality documentation, including timestamped evidence of model execution, configuration identifiers, and applicable diagnostic groupings. Role-specific output generation may be implemented using a dynamic rendering layer within the user interface 124, a rules-based output filter, or a preconfigured set of display templates selected at runtime based on the authenticated user's access profile. In some cases, display templates may be dynamically adjusted based on session context, such as time of day, clinical urgency, or temporary escalation of user privileges during supervised review sessions. In some embodiments, users may toggle between role views or access additional detail by elevating their access level or linking to a full diagnostic report. This approach may allow system 100 to support diverse clinical roles without overloading users with irrelevant data, and enhance usability, workflow efficiency, and compliance with privacy or access-control policies.

Still referring to FIG. 1, in an embodiment, at least a processor 108 may be further configured to tailor a visualization of the unified output data structure 144 as a function of a role associated with a user accessing the user interface. As used herein, a "role" refers to a set of access privileges or clinical responsibilities associated with a particular user or user type. For example, such as a nurse, general practitioner, specialist, technician, or administrative staff member. In various embodiments, system 100 may determine the user's role based on login credentials, access control profiles, or session metadata. Tailoring the visualization may include modifying one or more display parameters of the unified output data structure, including without limitation the amount of information shown, the level of detail, the prioritization of diagnostic outputs, or the inclusion of advanced explanation layers. For example, a nurse may be presented with a high-level summary of key findings and risk alerts, while a cardiologist may receive detailed model-specific outputs, waveform explanations, and confidence indicators. In some embodiments, the user interface may dynamically adjust its layout, labeling, or interactivity as a function of the identified role. Role-specific views may be implemented through display templates, rules-based filters, or modular interface components that activate or suppress features according to predefined mappings. In certain embodiments, users may have the ability to toggle between views or request elevated access, subject to institutional policy and audit logging. This role-based visualization capability may enhance clinical efficiency, reduce cognitive load, and ensure that users receive only the information most relevant to their scope of practice.

In further reference to FIG. 1, in an embodiment, generation and presentation of role-specific output views may be governed by access control logic that enforces institutional policies, user authentication credentials, and data governance rules. System 100 may maintain a user profile or access credential for each authorized user, which may include one or more access control attributes, such as clinical role, department affiliation, clearance level, or scope of practice. These attributes may be used to determine which components of the unified output data structure 144 are rendered to the user interface 124, as well as which actions may be performed (e.g., acknowledging a high-risk finding, adding annotations, exporting results). For example, a technician may be permitted to view output summaries and monitor system status, while only a credentialed clinician may access detailed explanation layers or confirm model-driven clinical decisions. In some embodiments, institutional administrators may configure policies that override or refine default role behavior, such as restricting access to sensitive diagnostic outputs 152 based on patient status, location, or research designation. In an embodiment, each role-specific view may be logged along with metadata identifying the user, the time of access, and the elements of the output data that were rendered or interacted with. This access log may be stored for auditing purposes, regulatory compliance, or traceability in clinical review processes. In some configurations, audit records may include version tracking of the output data structure and user activity timestamps, enabling retrospective reconstruction of what was seen and acted upon during a given diagnostic session. This governance framework may allow system 100 to maintain robust access control while providing tailored diagnostic information to diverse users operating under institutional, regulatory, or legal constraints. In some configurations, audit records may be made accessible through an administrative interface, enabling authorized users to query, review, or export audit trails for internal oversight or regulatory inspection.

With further reference to FIG. 1, in an embodiment, outputting the unified output data structure 144 may include dynamically surfacing one or more components of the unified output data structure 144 at a user interface 124 configured for interactive review. In an embodiment, system 100 may parse the data structure into discrete visual modules or panels, each corresponding to a diagnostic output from a specific AI model and present these modules in an organized layout grouped by diagnostic category 168, model type, or clinical priority. The interface may highlight high-risk results, update displays in real time as models complete execution, and allow for sorting or filtering based on parameters such as likelihood score 164, confidence interval, or disease category. In some embodiments, the unified output data structure 144 may be visually segmented into tiers. For example, a top-level composite risk profile 176, followed by diagnostic outputs 152 grouped by severity or system (e.g., cardiovascular, pulmonary). Interactive controls may allow the user to drill down into each output, revealing explanation layers, metadata, or prior diagnostic history when available. The user interface 124 may also support toggling between raw output values and clinically interpreted views, enhancing accessibility for both specialist and non-specialist users. In an embodiment, the user interface 124 may be configured to render these results across a range of devices, including desktop workstations, tablets, or mobile devices, with responsive formatting optimized for screen size, role-based access, and institutional workflow settings. In some embodiments, system 100 may synchronize a user's current view state across sessions or devices, allowing clinicians to resume review from another authenticated location without data loss. The interface may further support bookmarking or saving filtered result sets for follow-up action or case review. Output elements may be cached locally or retrieved on demand based on user navigation and session state.

Figure 2:
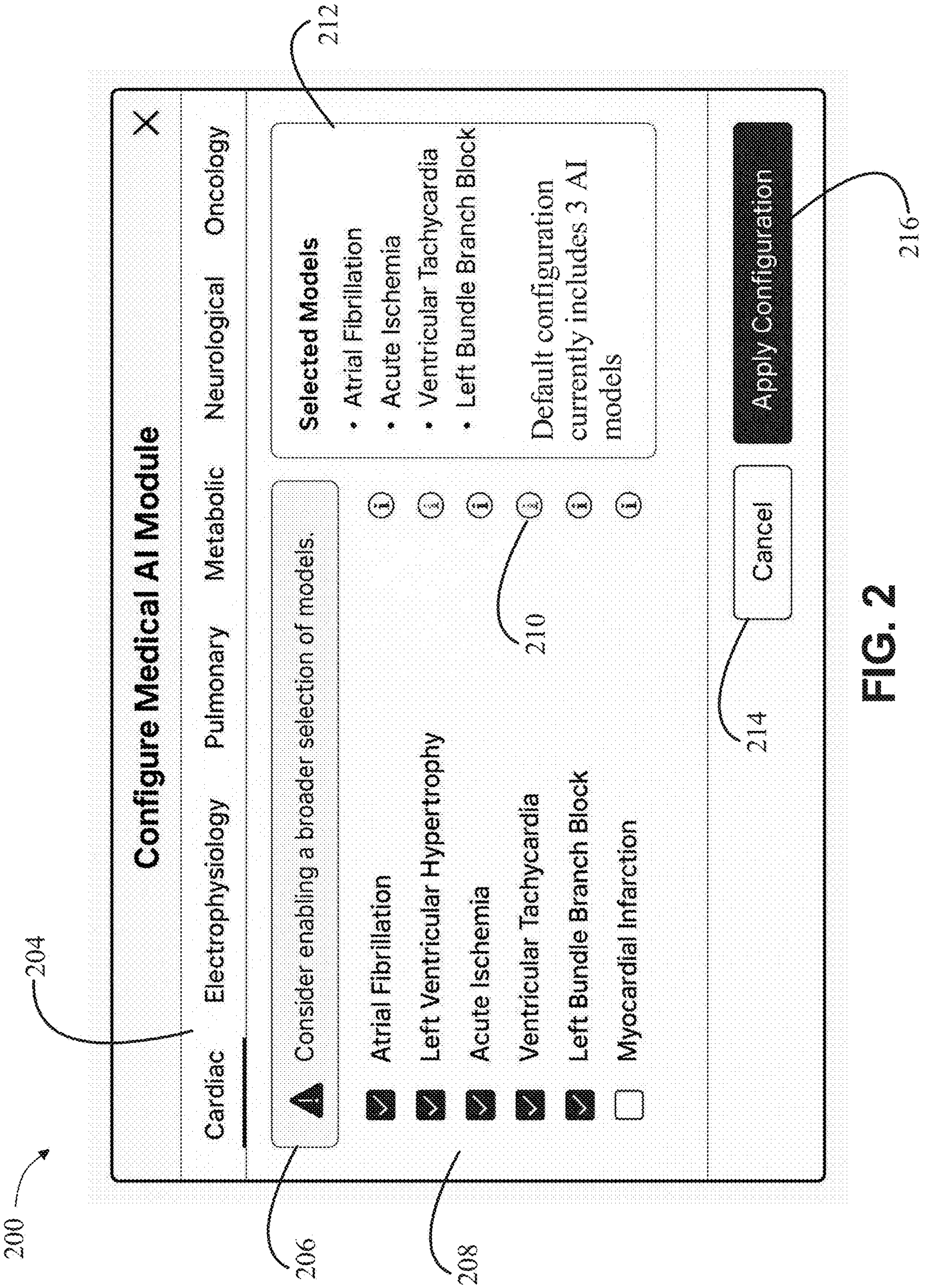
FIG. 2 illustrates an exemplary embodiment of a user interface displaying a customizable user interface for generating a configuration signal.

Referring now to FIG. 2, illustrated is an exemplary embodiment of a user interface 200 displaying a customizable user interface for generating a configuration signal. In an embodiment, user interface 200 may be clinician-facing and enable a user to configure a medical AI module by enabling or disabling specific AI models associated with one or more diagnostic categories. User interface 200 may include a category tab bar 204 positioned near the top of the interface. In an embodiment, category tab bar 204 may display multiple selectable diagnostic categories, such as "Cardiac," "Electrophysiology," "Pulmonary," "Metabolic," "Neurological," and "Oncology." Selection of one of the category tabs may filter the list of available AI models to only those relevant to the chosen diagnostic domain. In the illustrated embodiment, the "Cardiac" tab is active. Beneath category tab bar 204 is a configuration prompt banner 206, which in this example displays a system-generated recommendation to "Consider enabling a broader selection of models." In some embodiments, configuration prompt banner 206 may be generated in response to predefined thresholds, such as when the number or diversity of selected models is below an institutional guideline or based on patient-specific context.

In further reference to FIG. 2, in an embodiment, a model selection panel 208 is shown on the left side of the interface. Model selection panel 208 may include a list of AI models available within the currently selected diagnostic category. Each model listing may include a selectable checkbox for activation or deactivation, a model name (e.g., "Atrial Fibrillation," "Acute Ischemia"), and an information icon 210 that may be used to display additional metadata about the corresponding model. In some embodiments, this metadata may include model version, training cohort description, performance benchmarks, or links to associated explanatory documentation. To the right of model selection panel 208 is a selected model summary panel 212. Selected model summary panel 212 may list all AI models currently selected by the user for inclusion in the configuration. It may also display a description of the default configuration, including the number of models originally selected by the system (e.g., "Default configuration currently includes 3 AI models").

With further reference to FIG. 2, in an embodiment, at the bottom of user interface 200, action controls may be provided including a cancel button 214 and an apply configuration button 216. In an embodiment, cancel button 214 may discard user modifications and close the configuration interface. Apply configuration button 216 may save the current selection of models and apply the configuration to the medical AI module for execution on an input dataset such as an ECG signal.

The embodiment shown in FIG. 2 may enable user-driven customization of AI model execution workflows. In other embodiments, this configuration interface may include suggested models based on predefined associations, historical usage patterns, or inferred patient risk factors. The configuration process may be used to construct tailored diagnostic panels that reflect both institutional practices and individual patient context.

Figure 3:
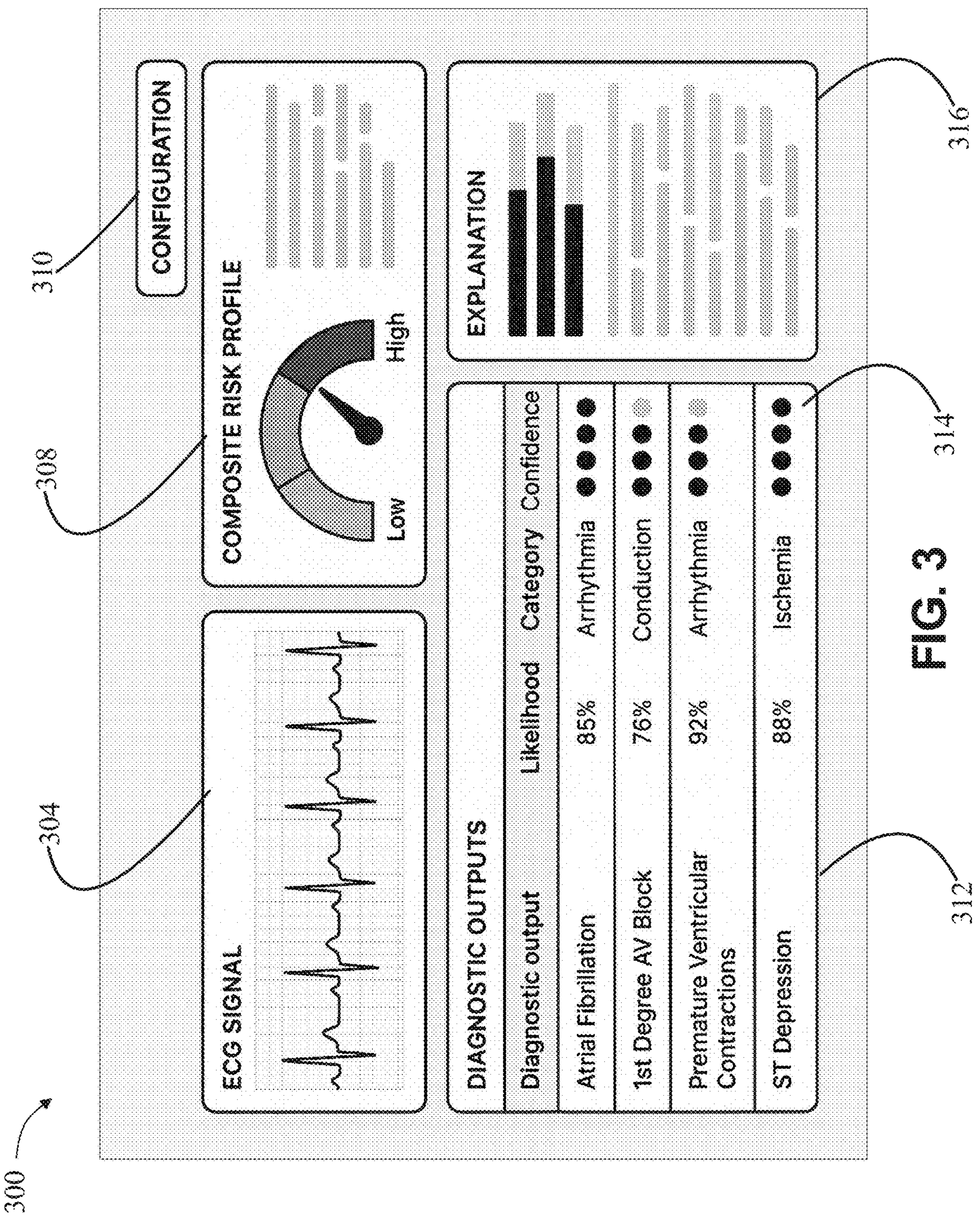
FIG. 3 illustrates an exemplary embodiment of a user interface displaying a unified output data structure.

Now referring to FIG. 3, illustrated is an exemplary embodiment of a user interface 300 displaying a unified output data structure. In an embodiment, user interface 300 may include a clinician-facing user interface for presenting diagnostic results generated by a configurable set of AI models operating on an ECG signal. In an embodiment, user interface 300 may include an ECG signal display 304, which may present a visual rendering of the ECG waveform data analyzed by the system. In some embodiments, ECG signal display 304 may render a single lead or multiple leads, and may be scrollable, zoomable, or annotated with features extracted by one or more AI models. To the right of ECG signal display 304, a composite risk profile area 308 is shown. Composite risk profile area 308 may include a graphical gauge representing an overall risk level based on an aggregation of diagnostic outputs from the configured AI models. The risk indicator may be supplemented by a summary of contributing diagnostic categories or severity assessments, either in textual or graphical form.

With continued reference to FIG. 3, in an embodiment, configuration control 310 may be located in the upper right portion of the interface. Configuration control 310 may be a button, icon, or link that allows the user to access a configuration interface, such as that described in FIG. 2, for modifying the AI model selection or viewing patient-specific default settings. In an embodiment, a diagnostic output panel 312 is shown below the ECG waveform and composite risk profile areas. Diagnostic output panel 312 may include a structured table including multiple rows, each corresponding to an AI model result. For each row, the table may display: (i) the diagnostic output label (e.g., Atrial Fibrillation), (ii) a likelihood score, (iii) a diagnostic category (e.g., Arrhythmia, Conduction), and (iv) a confidence indicator 314. Confidence indicator 314 may be rendered using graphical icons such as filled dots, bars, or other symbols indicating the model's certainty or prediction strength.

In further reference to FIG. 3, in an embodiment, to the right of diagnostic output panel 312, user interface 300 may include an explanation panel 316. Explanation panel 316 may include one or more graphical bars, visualizations, or charts indicating the most significant contributing features that influenced a particular model's output. Below the graphical display, a textual summary may explain which aspects of the ECG signal or patient characteristics contributed to the result, such as waveform abnormalities, rhythm irregularities, or known clinical risk factors.

With continued reference to FIG. 3, although not explicitly illustrated, in some embodiments, user interface 300 may further include interactive features such as model selection filters, result sorting options, export buttons, annotation tools, or integration links to electronic health record (EHR) platforms. Additionally, individual output rows within diagnostic output panel 312 may support click-to-expand behavior, allowing access to deeper explanation layers, historical comparisons, or model performance metrics. The embodiment shown in FIG. 3 provides a structured and interpretable interface for displaying AI-derived diagnostic information based on a patient's ECG signal. By surfacing both summary-level insights and detailed model-specific outputs, user interface 300 may support enhanced clinical decision-making, facilitate early intervention, and promote transparency in the use of AI-assisted diagnostics.

Figure 4:
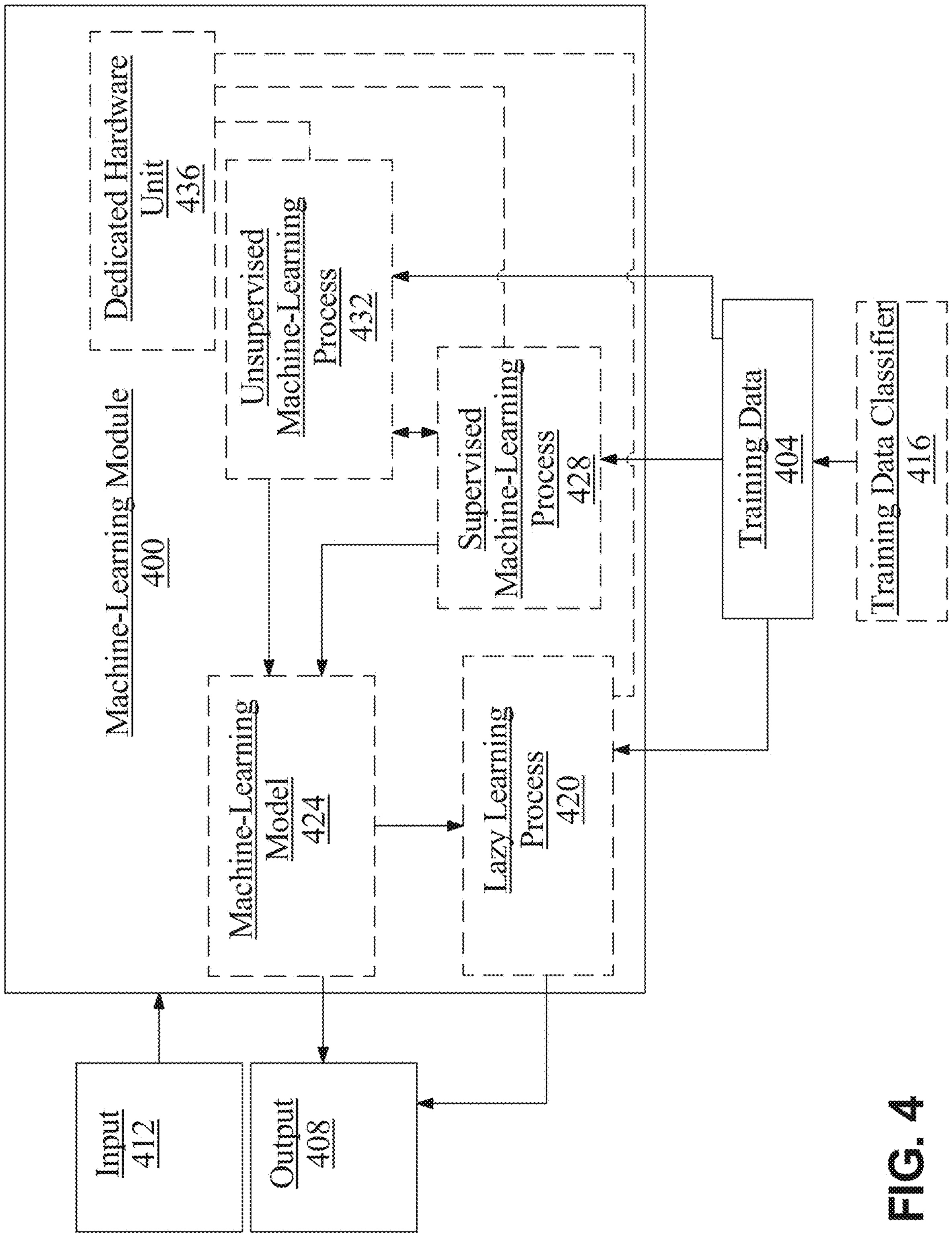
FIG. 4 is a block diagram of an exemplary machine-learning process.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm instantiated in hardware or software logic, data structures, and/or functions that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example input data may include ECG signals collected from patients with varied cardiovascular and systemic conditions, and output data may include structured labels corresponding to diagnostic outcomes, disease severity classifications, or risk stratification scores suitable for supervised training of the disease-specific AI models.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to identify sub-populations of patients exhibiting similar ECG signal morphologies, comorbidity patterns, or clinical outcomes, thereby allowing for selection of a subset of training data used to train disease-specific models targeting particular cardiac conditions or risk stratification levels.

Still referring to FIG. 4, a computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)+P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. A computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 4, a computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 4, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 4, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. A computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 4, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 4, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 4, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 4, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 4, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 4, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 4, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation a of a set or subset of values:

$$X_{new} = \frac{X - X_{mean}}{\sigma}.$$

Scaling may be performed using a median value of a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 4, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs as described above as inputs, outputs described above as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

With further reference to FIG. 4, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Continuing to refer to FIG. 4, evaluation of error function and/or other comparison results may include comparison of each of error function and/or other comparison results to a maximum single error threshold; in other words, a criterion of evaluation may include performing iterative retraining if any single comparison and/or error function output exceeds maximum single error threshold or if a count of single comparison and/or error function outputs exceeding single error threshold exceeds a threshold number and/or proportion of overall error function and/or other comparison results. Alternatively or additionally, evaluation of error function and/or other comparison results may include comparison of an aggregated plurality of error function and/or other comparison results to an aggregate error threshold; in other words, a criterion of evaluation may include performing iterative retraining if a result of averaging or otherwise aggregating a plurality such as some or all evaluated function and/or other comparison results exceeds aggregate error threshold. Aggregation may be performed in any manner of aggregation described in this disclosure and/or any combination thereof. Criteria for evaluations may be evaluated separately such that failing any one criterion causes iterative retraining; alternatively or additionally evaluation results may be combined according to one or more logical or other rules.

As a non-limiting, illustrative example, and still referring to FIG. 4, where outputs to be compared by error function are numerical values, error function may include subtraction of one from the other to derive an absolute value and/or mean squared error. Where outputs and/or training examples are represented as a binary classification, an error function may include a hinge loss function, sigmoid cross entropy loss function, weighted cross entropy loss function, or the like. Where output and/or exemplary output in a training set is a classification to three or more values, error function may include a softmax cross entropy loss function, a sparse cross entropy loss function, a Kullback-Leibler divergence loss function, or the like. Where both retaining and training with include supervised training, retraining may use a different error function, different weight update functions and/or parameters, or the like than in the training stage. For instance, and without limitation, when a previous iterative retraining process included training using examples from until a first convergence threshold and/or epsilon value and/or neighborhood is met, a subsequent iterative retraining process may include a lower convergence threshold, a smaller value of epsilon, or the like. Iterative retraining may include using one or more examples that were not used in any previous training and/or retraining process; for instance, where convergence was initially and/or previously achieved using a first subset of examples a subsequent retraining process may use examples from a second subset of examples, which may be wholly disjoint from first subset and/or have one or more elements that are not found in first subset.

Still referring to FIG. 4, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 432 may not require a response variable; unsupervised processes 432 may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 4, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic “1” and “0” voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 4, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 4, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 4, one or more processes or algorithms described above may be performed by at least a dedicated hardware unit 436. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 436 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 436 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 436 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 5:
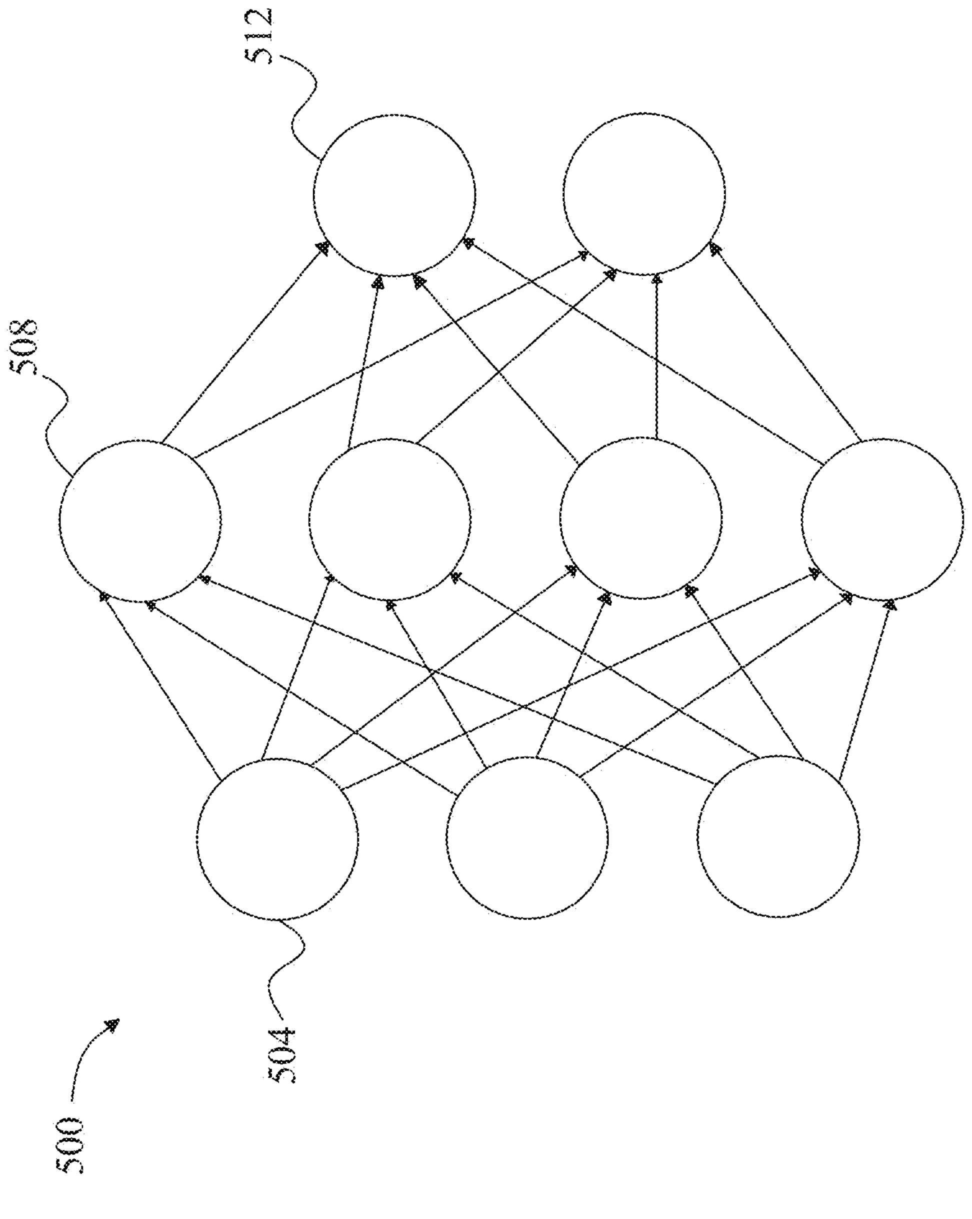
FIG. 5 is a diagram of an exemplary embodiment of a neural network.

Referring now to FIG. 5, an exemplary embodiment of neural network 500 is illustrated. A neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 6:
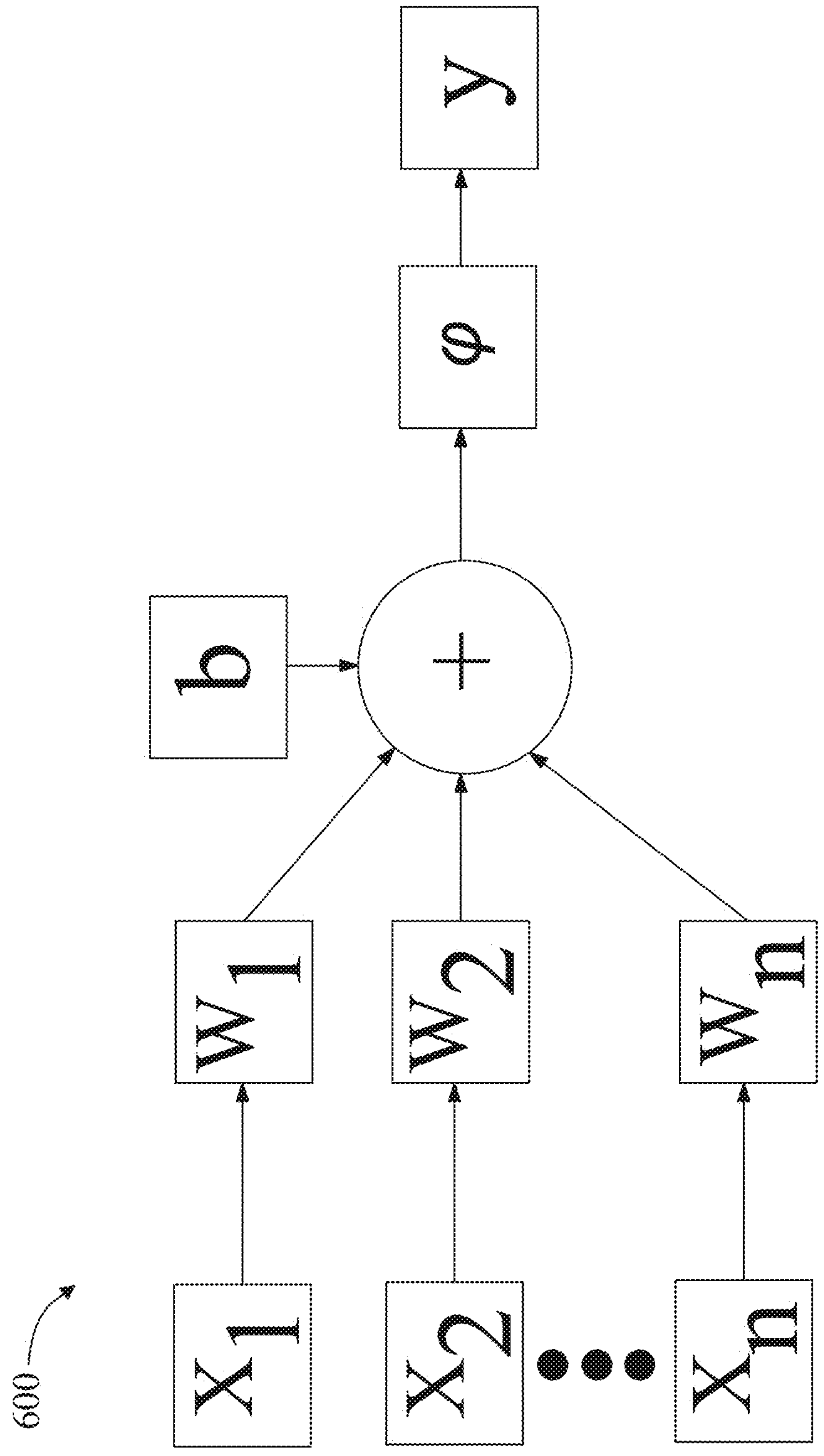
FIG. 6 is a diagram of an exemplary embodiment of a node of a neural network.

Referring now to FIG. 6, an exemplary embodiment of a node 600 of a neural network is illustrated. A node may include, without limitation a plurality of inputs xi that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as f(x)=max(0, x), a "leaky" and/or "parametric" rectified linear unit function such as f(x)=max (ax, x) for some a, an exponential linear units function such as $$f(x) = \begin{cases} x \text{ for } x \geq 0 \\ \alpha(e^x - 1) \text{ for } x < 0 \end{cases}$$

for some value of a (this function may be replaced and/or weighted by its own derivative in some embodiments), a softmax function such as $$f(x_i) = \frac{e^x}{\sum_i x_i}$$

where the inputs to an instant layer are xi, a swish function such as f(x)=x*sigmoid(x), a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda\begin{cases} \alpha(e^x - 1) \text{ for } x < 0 \\ x \text{ for } x \geq 0 \end{cases}.$$

Fundamentally, there is no limit to the nature of functions of inputs xi that may be used as activation functions. As a non-limiting and illustrative example, node may perform a weighted sum of inputs using weights $w_i$ that are multiplied by respective inputs xi. Additionally, or alternatively, a bias b may be added to the weighted sum of the inputs such that an offset is added to each unit in the neural network layer that is independent of the input to the layer. The weighted sum may then be input into a function p, which may generate one or more outputs y. Weight $w_i$ applied to an input xi may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$, or of other coefficients and/or parameters of an activation function, may be determined by training a neural network using training data, which may be performed using any suitable process as described above. Each weight in a neural network may, without limitation, be updated and/or tuned, based on an error function J, using a backpropagation updating method, such as:

$$w_{new} = w_{old} - \alpha\frac{dJ}{dw}$$

where $w_{new}$ is the updated weight value, $w_{old}$ is the previous weight value, α is a parameter to set the learning rate, and $$\frac{dJ}{dw}$$

is the partial derivative of with respect to weight w.

Figure 7:
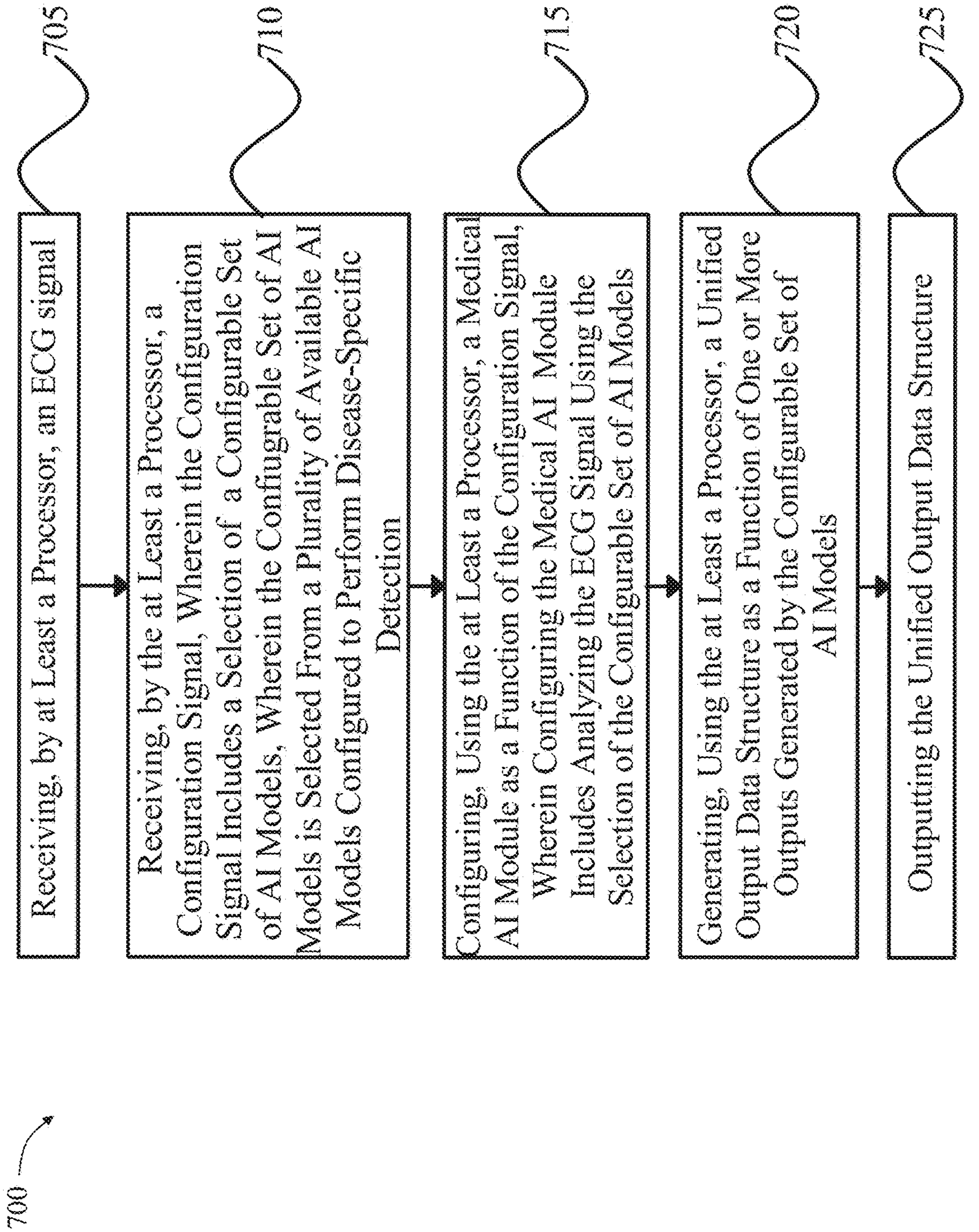
FIG. 7 is a flow diagram of an exemplary embodiment of a method for generating diagnostic information as a function of an ECG signal.

Referring now to FIG. 7, illustrated is an exemplary method 700 for generating diagnostic information as a function of an ECG signal. Method 700 may include a step 705 of receiving an ECG signal. This may be implemented, without limitation, as referenced in FIGS. 1-6.

In further reference to FIG. 7, method 700 may include a step 710 of receiving, using a user interface, a configuration signal. In an embodiment, the user interface may be configured to display a plurality of selectable AI models grouped under disease category labels. In an embodiment, the configuration signal may include a selection of a configurable set of AI models, wherein the configurable set of AI models is selected from a plurality of available AI models configured to perform disease-specific detection. In an embodiment, the configurable set of AI models may include at least one model configured to detect a presence of a disease and at least one model configured to predict a severity of the disease. In an embodiment, at least one AI model of the configurable set of AI models has been trained on a disease-specific training dataset. In an embodiment, the configurable set of AI models may include two or more linked models, wherein a result generated by a first model is used to trigger execution of a second model. This may be implemented, without limitation, as referenced in FIGS. 1-6.

With continued reference to FIG. 7, method 700 may include prompting a user, in response to the configuration signal, to additionally select one or more related AI models as a function of a predefined association between the selection of a configurable set of AI models and other models within the plurality of available AI models. This may be implemented, without limitation, as referenced in FIGS. 1-6.

In continued reference to FIG. 7, method 7 may further include generating a default configuration of the configurable set of AI models as a function of one or more patient-specific characteristics. In an embodiment, generating a default configuration may include identifying one or more disease categories associated with the patient-specific characteristics. Further, in an embodiment, generating a default configuration may include selecting AI models from the plurality of available AI models as a function of identifying one or more disease categories. This may be implemented, without limitation, as referenced in FIGS. 1-6.

With continued reference to FIG. 7, method 700 may include a step 715 of configuring a medical AI module as a function of the configuration signal. In an embodiment, configuring the medical AI module may include analyzing the ECG signal using the selection of the configurable set of artificial intelligence models. This may be implemented, without limitation, as referenced in FIGS. 1-6.

In further reference to FIG. 7, method 700 may include a step 720 of generating a unified output data structure as a function of one or more outputs generated by the configurable set of AI models. In an embodiment, generating a unified output data structure may include receiving diagnostic outputs generated by each AI model of the configurable set of AI models, each diagnostic output including a model-specific result. Further, in an embodiment, generating a unified output data structure may include organizing the processed diagnostic outputs into a structured data collection.

In an embodiment, the user interface may display, for each diagnostic output, a likelihood score, a diagnostic category, and a confidence indicator associated with an AI model result. In an embodiment, the unified output data structure may include a composite risk profile generated by applying an aggregation function to the diagnostic outputs of the configurable set of AI models. This may be implemented, without limitation, as referenced in FIGS. 1-6.

With continued reference to FIG. 7, method 700 may include a step 725 of outputting the unified output data structure. This may be implemented, without limitation, as referenced in FIGS. 1-6.

In further reference to FIG. 7, method 700 may further include tailoring a visualization of the unified output data structure as a function of a role associated with a user accessing the user interface. This may be implemented, without limitation, as referenced in FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
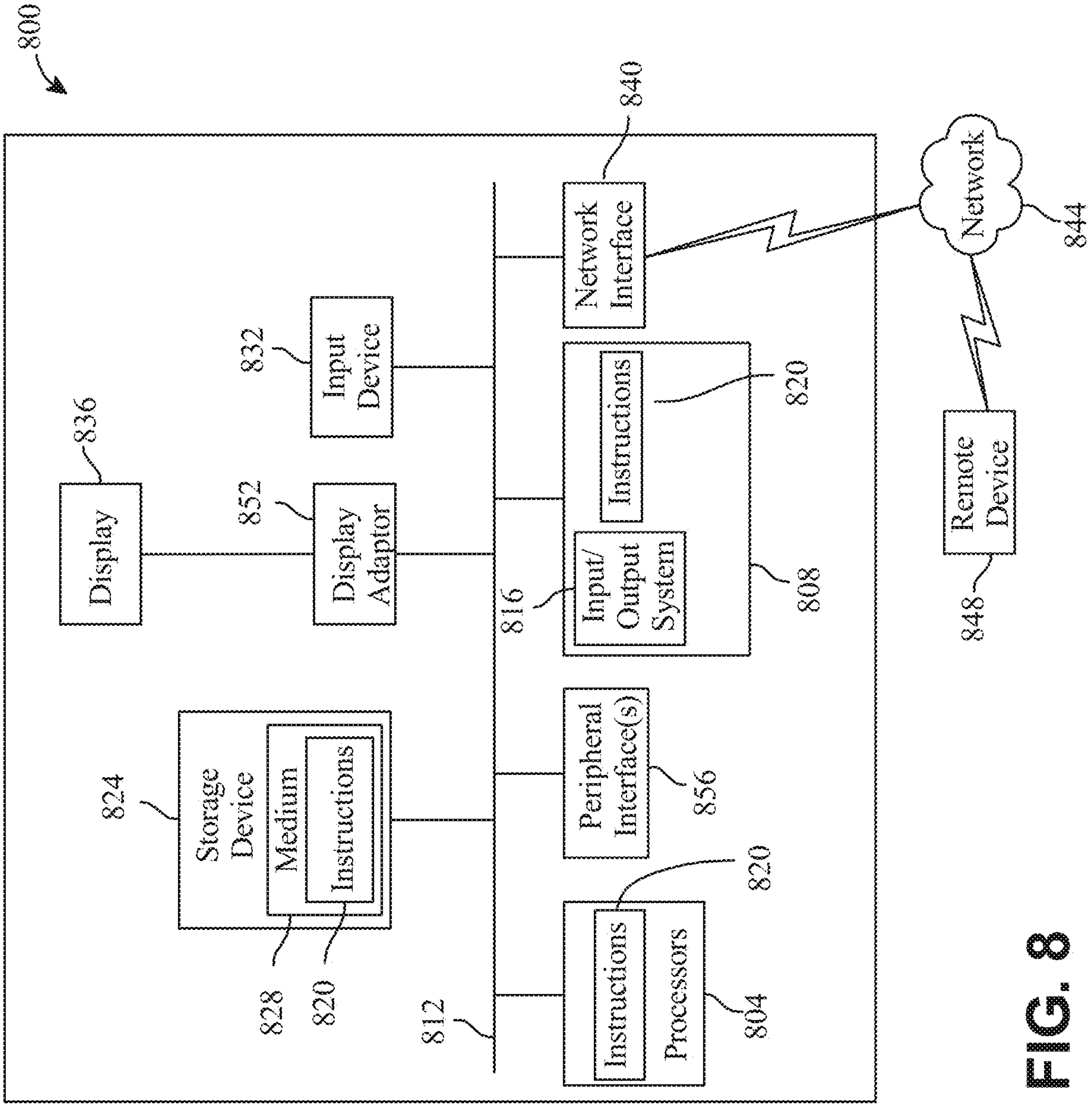
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display 836. Examples of a display device include, but are not limited to, a liquid crystal display (LCD), a cathode ray tube (CRT), a plasma display, a light emitting diode (LED) display, and any combinations thereof. Display adapter 852 and display 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating diagnostic information as a function of an electrocardiogram (ECG) signal, the system comprising:

at least a processor; and a memory communicatively connected to the at least a processor, wherein the memory contains instructions configuring the at least a processor to:

receive at least an ECG signal, wherein the at least an ECG signal corresponds to a single ECG acquisition of a single subject;

receive, using a user interface, a configuration signal, wherein the configuration signal comprises a selection of at least two artificial intelligence (AI) models, wherein the at least two AI models is selected from a plurality of available AI models configured to perform disease-specific detection and at least one AI model of the at least two AI models comprises a neural network configured to process the at least an ECG signal;

configure a medical AI module as a function of the configuration signal, wherein configuring the medical AI module comprises:

executing the at least two AI models under control of an orchestration layer configured to dynamically determine execution order between the at least two AI models as a function of features associated with the at least an ECG signal, wherein execution of a first AI model triggers execution of a second AI model based on a result generated by the first AI model; and analyzing the at least an ECG signal using the selection of the at least two AI models;

generate a unified output data structure as a function of one or more outputs generated by the at least two AI models, wherein generating a unified output data structure comprises:

receiving a plurality of diagnostic outputs generated by each AI model of the at least two AI models, each diagnostic output comprising a model-specific result; and organizing the plurality of diagnostic outputs into a structured data collection by generating a composite risk profile by aggregating likelihood scores and confidence metrics associated with the plurality of diagnostic outputs of each of the at least two AI models, wherein the aggregation comprises weighted summation of the likelihood scores and the confidence metrics; and output the unified output data structure.

2. The system of claim 1, wherein the at least a processor is further configured to display through the user interface, for each diagnostic output, a likelihood score and a diagnostic category associated with an AI model result.

3. The system of claim 1, wherein the user interface is configured to display a plurality of selectable AI models grouped under disease category labels.

4. The system of claim 1, wherein the unified output data structure comprises the composite risk profile generated by applying an aggregation function to the plurality of diagnostic outputs of the at least two AI models.

5. The system of claim 1, wherein the at least two AI models comprises at least one model configured to detect a presence of a disease and at least one model configured to predict a severity of the disease.

6. The system of claim 1, wherein:

at least one AI model of the at least two of AI models has been trained on a disease-specific training dataset; and the at least a processor is further configured to:

receive feedback associated with the plurality of diagnostic outputs and associated explanations; and guide retraining of the at least two AI models and adaptation of model selection logic as a function of the feedback aggregated across multiple users.

7. The system of claim 1, wherein the at least a processor is further configured to, in response to the configuration signal, prompt a user to additionally select one or more related AI models as a function of a predefined association between the selection of the at least two AI models and other models within the plurality of available AI models.

8. The system of claim 1, wherein the at least a processor is further configured to generate a default configuration of the at least two AI models as a function of one or more patient-specific characteristics.

9. The system of claim 8, wherein generating the default configuration comprises:

identifying one or more disease categories associated with the patient-specific characteristics; and selecting AI models from the plurality of available AI models as a function of identifying one or more disease categories.

10. The system of claim 1, wherein the at least a processor is further configured to tailor a visualization of the unified output data structure as a function of a role associated with a user accessing the user interface.

11. A method for generating diagnostic information as a function of an electrocardiogram (ECG) signal, the method comprising:

receiving, by at least a processor, at least an ECG signal, wherein the at least an ECG signal corresponds to a single ECG acquisition of a single subject;

receiving, using a user interface, a configuration signal, wherein the configuration signal comprises a selection of at least two artificial intelligence (AI) models, wherein the at least two AI models is selected from a plurality of available AI models configured to perform disease-specific detection and at least one AI model of the at least two AI models comprises a neural network configured to process the at least an ECG signal;

configuring, using the at least a processor, a medical AI module as a function of the configuration signal, wherein configuring the medical AI module comprises:

executing the at least two AI models under control of an orchestration layer configured to dynamically determine execution order between the at least two AI models as a function of features associated with the at least an ECG signal, wherein execution of a first AI model triggers execution of a second AI model based on a result generated by the first AI model; and analyzing the at least an ECG signal using the selection of the at least two AI models;

generating, using the at least a processor, a unified output data structure as a function of one or more outputs generated by the at least two AI models, wherein generating a unified output data structure comprises:

receiving a plurality of diagnostic outputs generated by each AI model of the at least two of AI models, each diagnostic output comprising a model-specific result; and organizing the plurality of diagnostic outputs into a structured data collection by generating a composite risk profile by aggregating likelihood scores and confidence metrics associated with the plurality of diagnostic outputs of each of the at least two AI models, wherein the aggregation comprises weighted summation of the likelihood scores and the confidence metrics; and outputting the unified output data structure.

12. The method of claim 11, further comprising displaying through the user interface, for each diagnostic output, a likelihood score and a diagnostic category, associated with an AI model result.

13. The method of claim 11, further comprising displaying at the user interface a plurality of selectable AI models grouped under disease category labels.

14. The method of claim 11, further comprising generating the composite risk profile contained within the unified output data structure by applying an aggregation function to the plurality of diagnostic outputs of the at least two AI models.

15. The method of claim 11, wherein the at least two AI models comprises at least one model configured to detect a presence of a disease and at least one model configured to predict a severity of the disease.

16. The method of claim 11, wherein further comprising:

receiving feedback associated with the plurality of diagnostic outputs and associated explanations; and guiding retraining of the at least two AI models and adaptation of model selection logic as a function of the feedback aggregated across multiple users, wherein at least one AI model of the at least two of AI models has been trained on a disease-specific training dataset.

17. The method of claim 11, further comprising prompting a user in response to the configuration signal to additionally select one or more related AI models as a function of a predefined association between the selection of the at least two AI models and other models within the plurality of available AI models.

18. The method of claim 11, further comprising generating a default configuration of the at least two AI models as a function of one or more patient-specific characteristics.

19. The method of claim 18, wherein generating the default configuration comprises:

identifying one or more disease categories associated with the patient-specific characteristics; and selecting AI models from the plurality of available AI models as a function of identifying one or more disease categories.

20. The method of claim 11, further comprising tailoring a visualization of the unified output data structure as a function of a role associated with a user accessing the user interface.

* * * * *